(12) United States Patent
Leif

(10) Patent No.: US 8,501,096 B2
(45) Date of Patent: Aug. 6, 2013

(54) CENTRIFUGAL CYTOLOGY SYSTEM, CHAMBER BLOCK AND METHOD FOR THE PREPARATION OF TREATED MONOLAYERS OF SAMPLE MATERIAL

(76) Inventor: Robert Cary Leif, San Diego, CA (US)

( * ) Notice: Subject to any disclaimer, the term of this patent is extended or adjusted under 35 U.S.C. 154(b) by 1632 days.

(21) Appl. No.: 10/512,337

(22) PCT Filed: Apr. 14, 2003

(86) PCT No.: PCT/US03/11394
§ 371 (c)(1),
(2), (4) Date: Jul. 26, 2005

(87) PCT Pub. No.: WO03/104801
PCT Pub. Date: Dec. 18, 2003

(65) Prior Publication Data
US 2005/0260100 A1   Nov. 24, 2005

Related U.S. Application Data

(60) Provisional application No. 60/372,549, filed on Apr. 13, 2002.

(51) Int. Cl.
*G01N 9/30* (2006.01)
(52) U.S. Cl.
USPC ............. 422/72; 422/548; 422/535; 422/561; 422/510
(58) Field of Classification Search
USPC ................. 210/781, 782; 118/52; 436/45; 422/72, 503, 534
See application file for complete search history.

(56) References Cited

U.S. PATENT DOCUMENTS

| | | | |
|---|---|---|---|
| 3,856,470 A | 12/1974 | Cullis et al. | |
| 3,883,305 A | 5/1975 | Hoskins et al. | |
| 4,119,407 A | 10/1978 | Goldstein et al. | |
| 4,192,250 A | 3/1980 | van Duijn | |
| 4,234,539 A | 11/1980 | Ginsberg et al. | |
| 4,250,830 A | 2/1981 | Leif | |
| 4,306,514 A | 12/1981 | Bouclier | |
| 4,314,523 A | 2/1982 | Boeckel et al. | |
| 4,327,661 A | 5/1982 | Boeckel | |

(Continued)

OTHER PUBLICATIONS

G. N. Papanicolaou, ATLAS of Exfoliative Cytology, Published for the Commonwealth Fund by Harvard University Press. (1954).

(Continued)

*Primary Examiner* — Sally Merkling
(74) *Attorney, Agent, or Firm* — R. Scott Kimsey

(57) ABSTRACT

An apparatus and method for the automated preparation of treated monolayers of sample material, comprising: a centrifuge having a rotor (12) carrying removable chamber blocks (14); sample and reagent dispensers (26) and control systems (20). First, centrifugal force sediments sample material discretely to form a monolayer onto a receiving surface member (32) on one of the chamber blocks (14), while the same centrifugal force opens a valve (48) in the chamber block (14) to drain sample material. Then, centrifugal force delivers sequentially into discrete chamber blocks (14) discrete treating agents, during which time the sampler material monolayer is held in place on the receiving surface member (32) by centrifugal force. Then, each chamber block (14) is drained centrifugally through its already opened valve (48). Each treated sampler material is confined to an individual chamber block (14). Batch and random access delivery of treating agents can be employed. Each chamber block (14) includes separate inlets for the sample and treating agents.

14 Claims, 9 Drawing Sheets

U.S. PATENT DOCUMENTS

| | | | |
|---|---|---|---|
| 4,395,493 | A | 7/1983 | Zahniser et al. |
| 4,423,699 | A | 1/1984 | Boeckel et al. |
| 4,428,323 | A | 1/1984 | Wells |
| 4,431,606 | A | 2/1984 | Revillet et al. |
| 4,574,729 | A * | 3/1986 | Wells .............................. 118/52 |
| 4,576,110 | A * | 3/1986 | Wells .............................. 118/52 |
| 4,847,205 | A * | 7/1989 | Burtis et al. .................... 436/45 |
| 5,143,627 | A | 9/1992 | Lapidus et al. |
| 5,180,606 | A | 1/1993 | Stokes et al. |
| 5,188,935 | A | 2/1993 | Leif et al. |
| 5,282,978 | A | 2/1994 | Polk, Jr. et al. |
| 5,346,831 | A | 9/1994 | Carrico, Jr. et al. |
| 5,376,267 | A | 12/1994 | Stokes et al. |
| 5,419,279 | A | 5/1995 | Carrico, Jr. et al. |
| 5,474,687 | A * | 12/1995 | Van Vlasselaer ............. 210/782 |
| 5,480,484 | A | 1/1996 | Kelley et al. |
| 5,492,837 | A | 2/1996 | Naser-Kolahzadeh et al. |
| 5,503,802 | A | 4/1996 | Polk, Jr. et al. |
| 5,578,452 | A | 11/1996 | Shi et al. |
| 5,772,818 | A | 6/1998 | Polk, Jr. et al. |
| 5,784,193 | A | 7/1998 | Ferguson |
| 5,942,129 | A * | 8/1999 | Hayes ............................ 210/781 |
| 5,948,359 | A | 9/1999 | Kalra et al. |
| 6,010,909 | A | 1/2000 | Lapidus |

OTHER PUBLICATIONS

Hutchinson, M L. Isenstein L M. Goodman A. et al., "Homogeneous sampling accounts for the increased diagnostic accuracy using the ThinPrep.RTM. Processor", Am J. Clin. Path, vol. 101, pp. 215-219 (1994).

Tezuka, F. Shuki, H. Oikawa, H. et al., "Numerical counts of epithelial cells collected, smeared and lost in conventional Papanicolaou smear preparation", Acta Cytol., vol. 39, pp. 838-838 (1995).

Zahniser, D J. and Hurley, A A., "Automated Slide Preparation System for the Clinical Laboratory", Cytometry (Communications in Clinical Cytometry), vol. 26, pp. 60-64 (1996).

Leif, R C., "Methods for Preparing Sorted Cells as Monolayer Specimens". In Living Color, Protocols in Flow Cytometry and Cell Sorting, Eds. R. A. Diamond and S. DeMaggio, Springer, ISBN 3-540-65149-7, pp. 592-619, (2000).

Knesel, Jr. E A., Roche Image Analysis Systems, Inc. Acta Cytologica, vol. 40 pp. 60-66. (1996).

Garcia, G. L. and Tolles, W. E., "Ultrasonic Disaggregation of Cell Clusters", J. Histochem. Cytochem., vol. 25 pp. 508-512 (1977).

Rosenthal, D. L. Stern, E. McLatchie, C A. Lagasse, L D. Wall, R. and Castleman, K. R., "A Simple Method of Producing a Monolayer of Cervical Cells for Digital Image Processing", Anal. Quant. Cytol., vol. 1, pp. 84-88 (1979).

Voet L, Hannig K, and Zeiller K., "Cytofluorometric analysis of R-Thy-1. antigens in various rat lymphocytes with different electrophoretic mobility and organ distribution.", J Histochem Cytochem., vol. 27 pp. 426-431 (1979).

Leif, R C. Easter, Jr., H N. Warters, R L. et al. "Centrifugal cytology I. A quantitative technique for the preparation of glutaraldehyde-fixed cells for the light and scanning electron microscope", J. Histochem. Cytochem. vol. 19 pp. 203-215 (1971).

Schachman, H K., Ultracentrifugation in Biochemistry, pp. 25-31 (1959).

Leif, R C. "FDA 510K, Centrifugal Cytology" (1981).

Leif, R C. Chew, K L. King, E B. et al., "The Potential of Centrifugal Cytology Dispersions for Automated Cytology", in The Compendium on the Computerized Cytology and Histology (G. L. Wied, P. H. Bartels, D. L. Rosenthal, and U. Schenck Ed.). Tutorials of Cytology, Chicago III. (1994).

Leif, R C. Gall, S. Dunlap, L A. et al., "Centrifugal cytology IV: The preparation of fixed stained dispersions of gynecological cells", Acta Cytologica, vol. 19, pp. 159-168 (1975).

Leif, R C. Silverman, M. Bobbitt, D. et al., "Centrifugal Cytology: A New Technique for Cytodiagnosis", Laboratory Management, vol. 17, September: pp. 38-41 (1979).

Leif, R C. Bobbitt, D. Railey, C. et al., Centrifugal Cytology of Breast Aspirate Cells, Acta. Cytologica, vol. 24, pp. 255-261 (1980).

Bobbitt, D. Silverman, M. Ng, A B P. et al., "Centrifugal Cytology of Urine", Urology, vol. 28, pp. 432-433 (1986).

Stulting, R D. Leif, R C. Clarkson, J. et al., "Centrifugal Cytology of Ocular Fluids", Arch. Ophthalmol., vol. 100, pp. 822-825 (1982).

Thornthwaite, J T. and Leif, R C., "Plaque cytogram assay I. light and scanning electron microscopy of immunocompetent cells", J. Immunology, vol. 113, pp. 1897-1908 (1974).

Leif, R C. Hudson, J. Irvin II, G. et al., "The Identification by Plaque Cytogram Assays and BSA Density Distribution of Immunocompetent Cells", in Critical Factors in Cancer Immunology (J. Schultz and R. C. Leif Ed.), pp. 103-158. Academic Press, New York (1975).

Leif, R C. Ingram, D J. Bobbitt D. Gaddis, R. Nordqvist, S. and Ng, A B P., "Centrifugal Cytology, Dissociation and Staining of Gynecological Cells", In The Automation of Cancer Cytology and Cell Image Analysis, Edited by H. J. Pressman and G. L. Wied, Tokyo, pp. 53-62 (1979).

Leif, R C. Ingram, D. J. Clay, C. Bobbitt, D. Gaddis, R. Leif, S B. and Nordqvist, S., "Optimization of the Binding of Dissociated Exfoliated Cervico-Vaginal Cells to Glass Microscope Slides", J. Histochem. Cytochem. 25, pp. 538-543 (1977).

Kelln, N. and Loughlin, K. "Liquid Transfer Module for a Chemical Analyzer", U.S. Pat. No. 5,334,349 (1994).

Boon, M E. Kok, L P. Mango, L J. Rutenberg, A. and Rutenberg, M R. "Automated histological specimen classification system and method", U.S. Pat. No. 5,939,278 (1999).

Suurmeijera, A J H. and Boon M E. "Pretreatment in a High-pressure Microwave Processor for MIB-1 Immunostaining of Cytological Smears and Paraffin Tissue Sections to Visualize the Various Phases of the Mitotic Cycle", J. Histochem. Cytochem. 47, pp. 1015-1020 (1999).

* cited by examiner

Downfield 7 →

← 8 Upfield

Downfield 7 →
Fig. 6A
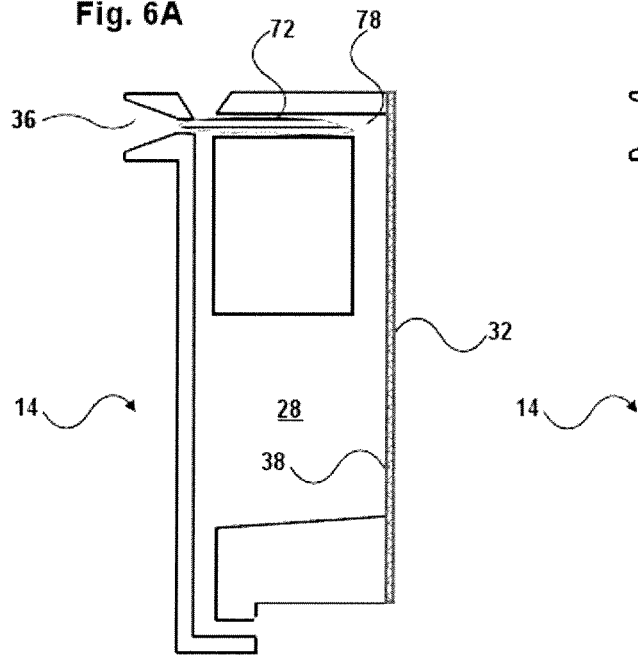
Fig. 6B
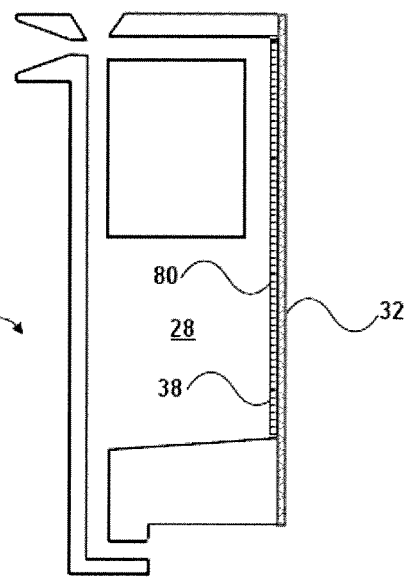
Fig. 6C
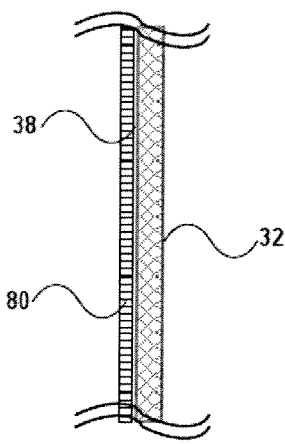
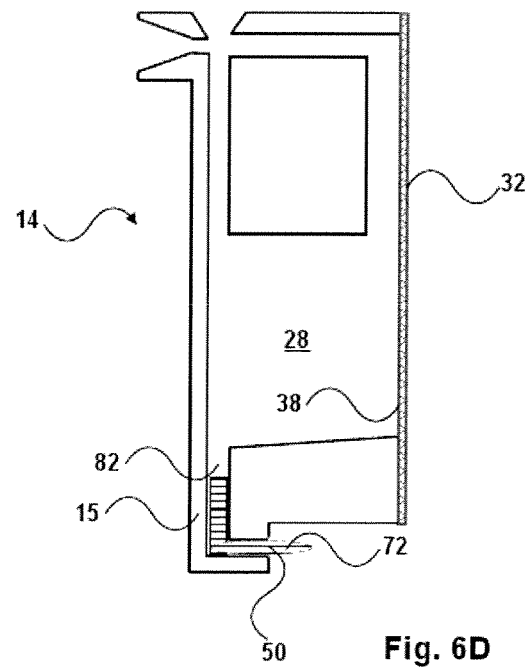
Fig. 6D
← 8 Upfield

CENTRIFUGAL CYTOLOGY SYSTEM, CHAMBER BLOCK AND METHOD FOR THE PREPARATION OF TREATED MONOLAYERS OF SAMPLE MATERIAL

The present Application claims priority of PCT Application No. PCT/US03/11394, entitled "Centrifugal Cytology System, Chamber Block and Method for the Preparation of Treated Monolayers of Sample Material" and filed Apr. 14, 2003, which Application in turn claims priority of U.S. Provisional Application No. 60/372,549, entitled "Device, Method and Process for the Preparation of Fixed, Stained Monolayer Preparations of Cells or Other Particles" and filed Apr. 13, 2002.

BACKGROUND OF THE INVENTION

Definitions

To facilitate understanding of the method of this invention, the following definitions of terms used in this specification and claims are provided.
1. The term "material" is defined to include: cells, organisms, bacteria, viruses, histological sections, organic and inorganic particulates and matter, and any other discernible material which provides diagnostic and/or analytical information whatsoever.
2. The term "microscopic analysis" is defined to be a process wherein a microscope under human and/or a machine control is used for visualization, analysis, and/or enumeration, and/or categorization, and/or photography, and/or electronic image acquisition of material.
3. The term "receiving surface member" will be used in a generic sense to describe all discrete objects which serve as substrates to support material for microscopic viewing and/or observation and/or analysis. The current, most common receiving surface member is a microscope slide, which is glass rectangular object that is approximately 1 mm thick, 25 mm wide, and 75 mm long. These are the items conventionally referred to as microscope slides for laboratory and commercial purposes.
4. The term "monolayer" is defined as a substantially two-dimensional layer of uniformly distributed material. For cytological applications, this material is predominantly made up of single cells and small clusters of cells, on a receiving surface member, such as a microscope slide or other appropriate substrate, without substantial folding or overlapping of cells or particles.
5. The term "specimen processor" will be used to describe a system that prepares one or more fixed, stained monolayer of material, such as cells or other particles, on receiving surface members.
6. The term "motor" is defined as an element or system that can index to specific angles and/or maintain rotatory motion.
7. The term "upfield direction" will be used to describe the direction opposite to the centrifugal field.
8. The term "downfield direction" will be used to describe the direction of the centrifugal field.
9. The term "random access" is defined in accordance with its use in clinical chemistry to be a process wherein one or more individual treating agents are delivered to specific members of a group of containers, such as: reaction containers, and/or sample containers, and/or chamber block assemblies, and/or cuvettes.
10. The term "batch" is defined in accordance with its use in clinical chemistry to be a process wherein one treating agent is delivered to all members of a group of containers, such as: reaction containers, and/or, sample containers, and/or chamber block assemblies, and/or cuvettes.
11. The term "stain" is defined to include any species that alters one or more optical properties of materials, such as cells or other particles. Thus, "stains" include: conventional small molecular histological or cytological stains such as DAPI, fluorescein, hematoxylin, europium Quantum Dye$^R$ and eosin. "Stains" also include macromolecular species, such as proteins, polysaccharides, RNA, and DNA that have been labeled with conventional stains, fluorescent macromolecules or contain an internal fluorochrome.
12. The term "treating agent" is defined to include any species or solution or fluid that alters one or more properties of materials. Thus, treating agents include: reagents; stains; buffers; fixatives; solvents, dehydrating and rehydrating liquids or solutions; lanthanide enhanced luminescence solutions; liquid coversliping solutions; cell permeating solutions; specific cell lysis solutions; gases; and molecules, particles or other cells that specifically combine with analytes present in or on the cells or other particles

Prior Art Citations

To facilitate a complete understanding of the Background of the Invention, as well as uses of the invention and its advantages over the prior art, numerous citations will be referenced (Ref.) by a number hereinafter, sometimes with page numbers and other times with direct quotation. These citations are sequentially numbered next.
1. G. N. Papanicolaou, "ATLAS of Exfoliative Cytology, Published for the Commonwealth Fund by Harvard University Press. (1954).
2. Hutchinson, M L. Isenstein L M. Goodman A. et al., "Homogeneous sampling accounts for the increased diagnostic accuracy using the ThinPrep® Processor", Am J. Clin. Path, Vol. 101, pp. 215-219 (1994).
3. Tezuka, F. Shuki, H. Oikawa, H. et al., "Numerical counts of epithelial cells collected, smeared and lost in conventional Papanicolaou smear preparation", Acta Cytol., Vol. 39, pp. 838-838 (1995).
4. Leif, R C., "Swinging Buckets (Centrifugal Cytology)", U.S. Pat. No. 4,250,830 (1981).
5. Zahniser, D J. and Hurley, A A., "Automated Slide Preparation System for the Clinical Laboratory", Cytometry (Communications in Clinical Cytometry), Vol. 26, pp. 60-64 (1996).
6. Leif, R C., "Methods for Preparing Sorted Cells as Monolayer Specimens". In Living Color, Protocols in Flow Cytometry and Cell Sorting, Eds. R. A. Diamond and S. DeMaggio, Springer, ISBN 3-540-65149-7, pp. 592-619, (2000).
7. Knesel, Jr. E A., Roche Image Analysis Systems, Inc. Acta Cytologica, Vol. 40 pp. 60-66. (1996).
8. Zahniser, D. J. and Garcia, G. L., "Monolayer device using filter techniques", U.S. Pat. No. 4,395,493 (1983).
9. Garcia, G. L. and Tolles, W. E., "Ultrasonic Disaggregation of Cell Clusters", J. Histochem. Cytochem., Vol. 25 pp. 508-512 (1977).
10. Rosenthal, D. L. Stern, E. McLatchie, C A. Lagasse, L D. Wall, R. and Castleman, K. R., "A Simple Method of Producing a Monolayer of Cervical Cells for Digital Image Processing", Anal. Quant. Cytol., Vol. 1, pp. 84-88 (1979).

11. Lapidus, S N. Polk, Jr., L T. Farber, F L. Barlas, J M. and Hurley, A A., "Method and Apparatus for Preparing Cells for Examination", U.S. Pat. No. 5,143,627 (1992).
12. Polk, Jr., L T. Bottomley, T E. and Brown, P P., "Specimen Processor Method and Apparatus", U.S. Pat. No. 5,282,978 (1994).
13. Polk, Jr., L T. Vartanian, H. Brown, P P. and Sloan, III, W M., "Apparatus for Collection and Transfer of Particles and Manufacture Thereof", U.S. Pat. No. 5,503,802 (1996).
14. Polk, Jr., L T. Vartanian, H. Brown, P P. and Sloan III, W M., "Apparatus for Collection and Transfer of Particles and Manufacture Thereof", U.S. Pat. No. 5,772,818 (1998).
15. Lapidus, S N., "Method and Apparatus for Controlled Instrumentation of Particles with a Filter Device", U.S. Pat. No. 6,010,909 (2000).
16. Carrico, Jr., C. L. Fox, W A. Geyer, J W. and Knesel, Jr., E A., "Cytorich Process System", U.S. Pat. No. 5,346,831 (1994).
17. Carrico, Jr., C L. Fox, W A. and Knesel, Jr., E A., "Apparatus for depositing and staining cytological material on a microscope slide", U.S. Pat. No. 5,419,279 (1995).
18. Voet L, Hannig K, and Zeiller K., "Cytofluorometric analysis of R-Thy-1. antigens in various rat lymphocytes with different electrophoretic mobility and organ distribution.", J Histochem Cytochem., Vol. 27 pp. 426-431 (1979).
19. Leif, R C. Easter, Jr., H N. Warters, R L. et al. "Centrifugal cytology I. A quantitative technique for the preparation of glutaraldehyde-fixed cells for the light and scanning electron microscope", J. Histochem. Cytochem. Vol. 19 pp. 203-215 (1971).
20. Schachman, H K., "Ultracentrifugation in Biochemistry, pp. 25-31 (1959).
21. Goldstein, R H. and Stahl, R M., "Cuvette with reagent release means", U.S. Pat. No. 4,119,407 (1978).
22. Leif, R C. "FDA 510K, Centrifugal Cytology" (1981).
23. Leif, R C. Chew, K L. King, E B. et al., "The Potential Of Centrifugal Cytology Dispersions For Automated Cytology", in The Compendium on the Computerized Cytology and Histology (G. L. Wied, P. H. Bartels, D. L. Rosenthal, and U. Schenck Ed.). Tutorials of Cytology, Chicago Ill. (1994).
24. Leif, R C. Gall, S. Dunlap, L A. et al., "Centrifugal cytology IV: The preparation of fixed stained dispersions of gynecological cells", Acta Cytologica, Vol. 19, pp. 159-168 (1975).
25. Leif, R C. Silverman, M. Bobbitt, D. et al., "Centrifugal Cytology: A New Technique for Cytodiagnosis", Laboratory Management, Vol. 17, September: pp. 38-41 (1979).
26. Leif, R C. Bobbitt, D. Railey, C. et al., "Centrifugal Cytology of Breast Aspirate Cells, Acta. Cytologica, Vol. 24, pp. 255-261 (1980).
27. Bobbitt, D. Silverman, M. Ng, A B P. et al., "Centrifugal Cytology of Urine", Urology, Vol. 28, pp. 432-433 (1986).
28. Stulting, R D. Leif, R C. Clarkson, J. et al., "Centrifugal Cytology of Ocular Fluids", Arch. Ophthalmol., Vol. 100, pp. 822-825 (1982).
29. Thornthwaite, J T. and Leif, R C., "Plaque cytogram assay I. light and scanning electron microscopy of immunocompetent cells", J. Immunology, Vol. 113, pp. 1897-1908 (1974).
30. Leif, R C. Hudson, J. Irvin II, G. et al., "The Identification by Plaque Cytogram Assays and BSA Density Distribution of Immunocompetent Cells", in Critical Factors in Cancer Immunology (J. Schultz and R. C. Leif Ed.), pp. 103-158. Academic Press, New York (1975).
31. Leif, R C. Ledis, S. and Fienberg, R., "A Reagent System and Method for Identification, Enumeration and Examination of Classes and Subclasses of Blood Leukocytes", U.S. Pat. No. 5,188,935 (1993).
32. Leif, R C. Ingram, D J. Bobbitt, D. Gaddis, R. Nordqvist, S. and Ng, A B P., "Centrifugal Cytology, Dissociation and Staining of Gynecological Cells", In The Automation of Cancer Cytology and Cell Image Analysis, Edited by H. J. Pressman and G. L. Wied, Tokyo, pp. 53-62 (1979).
33. van Duijn, P., "Valve-Centrifuge", U.S. Pat. No. 4,192,250, (1980).
34. Kelley, T F. and Floyd, A D., "Cytology Centrifuge Apparatus", U.S. Pat. No. 5,480,484 (1996).
35. Bouclier, R J., "Chamber with Removable Supernatant Collection Vial", U.S. Pat. No. 4,306,514 (1981).
36. Boeckel, J W., "Chamber Block Having a Supernatant Collection Receptacle Therein", U.S. Pat. No. 4,327,661 (1982).
37. Boeckel, J W., Rohde, V C., and Wells, J R., "Centrifuge Rotor Apparatus for Preparing Particle Spreads", U.S. Pat. No. 4,314,523 (1982).
38. Boeckel, J W., Rohde, V C., and Wells, J R., "Centrifuge Rotor Apparatus for Preparing Particle Spreads", U.S. Pat. No. 4,423,699 (1984).
39. Wells, J R., Chamber block having a sample dam and a supernatant reentry barrier therein, U.S. Pat. No. 4,428,323 (1984).
40. Wells, J R., "Rotor Having a Chamber Block with an Absorbant Plug", U.S. Pat. No. 4,576,110 (1986).
41. Wells, J R., "Chamber Block for a Cytocentrifuge Having Centrifugal Force Responsive Supernatant Withdrawal Means", U.S. Pat. No. 4,574,729 (1986)
42. Boeckel, J W. Rohde, V C. Wells, J. R., "Centrifuge Rotor Apparatus for Preparing Particle Spreads", U.S. Pat. No. 4,423,699 (1984).
43. Stokes, B O. and Quirante, C G., "Cytocentrifuge rotor for cytocentrifugation devices", U.S. Pat. No. 5,376,267 (1994).
44. Kalra, K L. Zhang, J Z. Chang, Z-W. and Shui, J., "Automated Staining Apparatus", U.S. Pat. No. 5,948,359 (1999).
45. Shi, S-R. Tandon, A K. Kalra, K L. Mallhotra, N. Su, S-H. Yu, C-Z., "Enhancement of Immunochemical Staining in Aldehyde-fixed Tissues", U.S. Pat. No. 5,578,452 (1996).
46. Zahra P N. and Stavrianopoulos, J G. Mounting Medium for Microscope Slide Preparations, U.S. Pat. No. 5,492,837 (1996).
47. Stokes, B O. Bradshaw, G D. Barlow, W K., "Apparatus for Applying a Controlled Amount of Reagent to a Microscope Slide or the Like", U.S. Pat. No. 5,180,606 (1993).
48. Cullis, H M. Fordham, W E. and Soodak, C I., "Rotor Apparatus", U.S. Pat. No. 3,856,470 (1974).
49. Revillet, G. and Thevoz, M., "Multicuvette Rotor for Analyzer", U.S. Pat. No. 4,431,606 (1984).
50. Ferguson, G W., "Microscope Slide with Removable Layer and Method", U.S. Pat. No. 5,784,193 (1998).
51. Leif, R C. Ingram, D. J. Clay, C. Bobbitt, D. Gaddis, R. Leif, S B. and Nordqvist, S., "Optimization of the Binding of Dissociated Exfoliated Cervico-Vaginal Cells to Glass Microscope Slides", J. Histochem. Cytochem. 25, pp. 538-543 (1977).
52. Ginsberg, G. Horne, T. and Kreiselman, R L., "Apparatus for Monitoring Chemical Reactions and Employing Moving Photometer Means", U.S. Pat. No. 4,234,539 (1980).
53. Hoskins, D H. Horne, T. Jarman, G R. and Dunsmore, W., "Automatic Chemical Analysis Apparatus", U.S. Pat. No. 3,883,305 (1975).

54. Kelln, N. and Loughlin, K. "Liquid Transfer Module for a Chemical Analyzer", U.S. Pat. No. 5,334,349 (1994).

55. Boon, M E. Kok, L P. Mango, L J. Rutenberg, A. and Rutenberg, M R. "Automated histological specimen classification system and method", U.S. Pat. No. 5,939,278 (1999).

56. Suurmeijera, A J H. and Boon M E. "Pretreatment in a High-pressure Microwave Processor for MIB-1 Immunostaining of Cytological Smears and Paraffin Tissue Sections to Visualize the Various Phases of the Mitotic Cycle", J. Histochem. Cytochem. 47, pp. 1015-1020 (1999).

1. Field of the Invention

This invention relates to an automated system that, from a sample of cells in a liquid medium, produces a monolayer preparation suitable for microscopic analysis.

2. Description of the Prior Art

G. N. Papanicolaou, for his clinical cytology studies, did not use the conventional smearing technique, classically used in hematology, to produce air-dried smears of cells. He stated (Ref. 1, p. 4), "Drying of the smears should be avoided throughout the procedure as it results in flattening and distortion of the cells and their nuclei and a loss of their structural characteristics and affinity for stains." This realization by Papanicolaou of the utility of wet fixation enabled him to start the field of cytological screening. The most successful use of cytological screening has been gynecological cytology.

The standard Papanicolaou wet fixed smear has the very significant problem of inadequate sampling of the material scraped from the cervix. Pap smears do not provide a representative sample of the sample obtained (Ref. 2 and Ref. 3). This has been solved as described in U.S. Pat. No. 4,250,830 (Ref. 4) by the transfer of the material to a liquid suspending medium and subsequent deposition of the cells on a receiving surface member. These liquid preparations have the further advantages of permitting the cell clumps to be partially disaggregated and monolayers to be formed with minimal adventitious cell overlap. They have the further advantage of permitting the sample to be separated into aliquots (split) to be used for multiple means for analysis. For instance, a first sample of a specimen containing gynecological cells can be used for conventional cervical cell microscopic screening and a second for clinical laboratory detection of an infecting organism, such as human papilloma virus.

Conventionally, after the cells have been deposited on the slide, the slides are then processed in groups. This processing includes changing of the stains and solvents, customarily by sequentially lifting one or more slides out of one vessel of treating agent and lowering them into a different vessel of treating agent. This has the significant problem that cells can fall off of a receiving surface member, such as a microscope slide, and even worse be transferred and adhere to a different receiving surface member. Since small numbers of abnormal individual cells or clumps of cells are all that is available and sufficient to make a diagnosis, the loss of these cells or clumps containing these cells from a receiving surface member can result in no evidence of disease when cancer cells were present in the sample. If these diagnostic cells instead of being lost from a first slide adventitiously attach to a second slide, then a false diagnosis of malignancy can occur.

The sum of the costs of processing of the cells to 1) produce monolayers, 2) stain and 3) apply a coverslip is sufficient to act as a deterrent to effective cancer screening. This is true even if each individual step includes automation.

Present Status of Exfoliative Cytology Monolayer Specimen Preparation Instrumentation The preparation of cells from a suspension on a receiving surface member, such as a microscope slide or similar receiving surface member, consists of the following steps:
(1) Obtain the sample;
(2) Suspend the sample in a solution, which often serves to fix and/or dissociate the cells;
(3) place the cells on a receiving surface member;
(4) stain the material on the receiving surface member;
(5) coverslip the receiving surface member;
(6) move one or more receiving surface members to a temporary storage device;
(7) transfer the receiving surface member to the microscope stage;
(8) analyze the material; and
(9) transfer the receiving surface member to an archive.

The three major factors controlling recovery of cells from a suspension onto a slide are: 1) cell losses in the apparatus; 2) the adhesiveness of the cell binding surface; and 3) the force pushing the cells onto the surface. The two basic methods for preparing monolayers are: 1) pressure transfer, where the cells are initially placed on a nonadhesive substrate and transferred by pressure to a slide which binds them (Ref. 5); and 2) centrifuging the cells onto a receiving surface member. (Ref. 6). One variation of centrifugation is to have the cells settle at unit gravity (Ref. 7).

Pressure Transfer

U.S. Pat. No. 4,395,493 (Ref. 8) is the first of a group of patents that describe a process for producing monolayers of cells by first collecting the cells from a sample suspension on a filter and then transferring the cells from the filter to a microscope slide with simultaneous fixation. This device is based on the initial studies of Garcia and Tolles (Ref. 9) and Rosenthal et al. (Ref. 10).

U.S. Pat. No. 4,395,493 teaches a device that consisted of: a cell suspension in a sample bath that under positive pressure delivered a cell containing suspension to conventional cell sensor, preferably an electronic cell counter, Coulter type. A control system metered this volume through the counter and into an application vessel, which had a rectangular window at its bottom which is closed by a filter strip or tape, which formed a water tight seal with a matching rectangular shaped top of a drain. This drain was connected to a vacuum source, which was activated while or after the sample suspension entered the vessel. This negative pressure sucked the liquid of the sample suspension through the tape or filter and deposited the cells on the upper surface of the tape. After withdrawing all liquid from vessel, the vacuum source was deactivated and the vessel drain and tape were separated.

The cell carrying tape was then advanced to a second location, where a conventional microscope slide is located on the cell-containing side of the tape; and a hard sponge, which has previously been wetted with fixative, is located on the opposite side of the tape. The block that supports the fixative containing sponge is moved in the direction of the microscope slide. This presses the hard sponge against the tape, thereby pressing the tape against the microscope slide. This facilitates the transfers of the cells to the slide and fixes them further. The inventors state, "not only fixes the cells, but helps them to adhere to the slide". (Col. 3, lines 39-40) The inventors provided an example of a fixative, which "contains in one liter: 95% ethanol (107.7 milliliters); distilled water (995.2 milliliters); sodium chloride (7.7 grams) and thymol (0.25 grams)." (Col. 3, lines 42-44) After the cells have been transferred, the sponge, tape, and slide are separated. Thereafter, the slide could be manually removed or transferred by some automated means "implemented by known devices in the art." (Col. 3, lines 50-51) The combination of standard or specialized robotics to transfer the microscope slide and the automated staining machine can be can be complex and is expensive in labor, capital cost, and bench space. The subsequent refinements of this invention, U.S. Pat. No. 4,395,493 (Ref. 8), to the CYTYC corporation, still have these problems and employ expensive filters. The CYTYC system has the problem of selective loss of cells and other diagnostic materials. This can occur by passage through the filter of small cells, bacteria, viruses, fibers, and particles, which can have diagnostic significance and selective transfer of the cells and other material from the tape to the slide.

Subsequent patents, U.S. Pat. No. 5,143,627 (Ref. 11) and U.S. Pat. No. 5,282,978 (Ref. 12) have described refinements, which include the use of a disposable sample collector with a complex mechanism to laterally and vertically move, rotate and invert it. The sample collector is terminated by either a circular or ellipsoidal filter. The sample collector is: 1) lowered into sample container with its filter end down; 2) rotated to induce a shear force, that disaggregated some of the clumps of cells; pumped under vacuum to selectively transfer the fluid that contains the cells from the sample container into the sample collector. This results in the cells being collected on the external surface of the filter. 3) The sample collector is then removed from the sample container and inverted. 4) A microscope slide is placed above the filter end of the sample collector; and 5) the cells are transferred from the surface of the filter to the microscope slide. This has been accomplished in two ways: either by applying alcohol to the inner surface of the filter, by action of an alcohol wetted sponge, or by air pressure applied to the inner side of the filter. Because of the critical nature of the contact between the filter and microscope slide, special manufacturing techniques, U.S. Pat. No. 5,503,802 (Ref. 13) and U.S. Pat. No. 5,772,818 (Ref. 14) have been developed to maintain the flatness of the filter and to provide a reliable seal between the filter and the body of the sample collector. In order to collect a selected quantity of cells for cytological examination, special means to provide feedback on the effect of the cells blocking the pores of the filter had to be developed, U.S. Pat. No. 6,010,909 (Ref. 15).

The systems described in the above patents are complex, involve significant numbers of moving parts including belts, and require a complex disposable, the sample collector, which includes an expensive filter. These systems only produce one cell dispersion at a time, are expensive; because their mechanical complexity results in significant maintenance costs; and requires ancillary expensive equipment, such as a slide stainer. In the case of air-driven dislodgement of the cells, air drying is possible. The dispersions of the slides produced have selected loss of particles smaller than the pore size of the filters; and the possibility of selective transfer of different types of cells from the filter to the slide can not be totally eliminated.

Unit Gravity Sedimentation

U.S. Pat. No. 5,346,831 (Ref. 16) describes a process for producing monolayers of cells on a cationically charged microscope slide. U.S. Pat. No. 5,346,831 states: "The method comprises the steps of separating the cytological material by centrifugation over a density gradient, producing a packed pellet of the cytological material, mixing the pellet of the cytological material, withdrawing an aliquot of a predetermined volume from the mixed pellet, depositing the aliquot and a predetermined volume of water into a sedimentation vessel, which is removably secured to the cationically-charged substrate, allowing the cytological material to settle onto the substrate under the force of gravity, and after settlement of the cytological material, removing the water from the sedimentation vessel. For automated analysis, the sedimentation vessel may be detached from the substrate." (Col. 2, Lines 7-21)

The sedimentation vessel and its use are described in U.S. Pat. No. 5,419,279 (Ref. 17). A cationically-charged, conventional microscope slide is sandwiched between a cylindrical tube and a base plate. The cylindrical tube has a flange at its base, which both holds an O-ring and locks into the base plate. A cylindrical chamber is formed by sealing the cylindrical tube to the conventional microscope slide surface with the O-ring. After a suspension of cells is added to the cylindrical chamber, the cells sediment under the earth's gravitational field and some settle and adhere to the slide. The supernatant solution is aspirated and then the cells are "stained using standard staining methods". (Col. 4, line 24)

U.S. Pat. No. 5,419,279 (Ref. 17) includes the statement, "After settlement of the cells onto the slide, the supernatant is removed by aspiration which also includes removal of excess cells which have not adhered to the slide." (Col. 4, lines 17-21) Since the cells in the sample either have not all sedimented on to the conventional microscope slide or have different surface charges (Ref. 18), which could result in differing capacities to adhere to the cationically-charged receiving surface of the receiving surface member (conventional microscope slide), the cells recovered on the slide need not be representative of the cells transferred to the cylindrical chamber.

U.S. Pat. No. 5,346,831 (Ref. 16) describes two centrifugation steps in 12 ml conical tubes followed by final resuspention of a small volume of sample, 150 ul, "followed by 500 ul of deionized $H_2O$ into a sedimentation vessel attached to a slide". (Col. 4, lines 48-49) This 650 ul is a smaller volume than is present in many samples, such as cervical scrapes.

Centrifuging the Cells

The first technique to prepare dispersions of wet fixed cells by centrifugation was centrifugal cytology (Ref. 19). The cells were centrifuged onto a conventional microscope slide, the supernatant removed and a fixative applied by a means that did not dislodge the cells. During fixation, the cells were held in position by the application of a centrifugal force. An apparatus used for this process is described in U.S. Pat. No. 4,250,830 (Ref. 4.), which is incorporated herein by reference. The design and use of an apparatus to perform centrifugal cytology has been described recently by Leif (Ref. 6), which is incorporated herein by reference. The present embodiment of the Leif Centrifugal Cytology bucket, as described in Ref. 6, is based on a swinging bucket rotor. Either an aluminum carrier serves as a replacement for the standard swing-out cup of a swinging bucket rotor, or a special plastic carrier is supported by a swing-cup of a swinging bucket rotor. In either case, a fluid tight chamber is formed by pressing and sealing an elastomeric chamber block against a standard 3 by 1 inch microscope slide (Ref. 4). The slide serves as the base of the pyramidal sample chambers present in the block. The incline of the slanted chamber walls follows the radius emanating from the center of the centrifuge. Since materials, such as cells and other particles, follow a radial trajectory, this incline prevents their deposition on the chamber walls. The cell containing suspension is first placed in a chamber and then the cells are centrifuged onto the slide. Most of the supernatant is removed and a fixative is added in a manner that does not dislodge the cells. A frit is used as a synthetic boundary valve, which limits the delivery of the bulk of the fixative to after the centrifugal field is applied. The designs of synthetic boundary cells, which are a means to transfer fluid in a centrifuge into a centrifugation chamber, have been described by Schachman (Ref. 20) and another design to deliver a reagent into a cuvette mounted in a centrifuge has been described by Goldstein et al. U.S. Pat. No. 4,119,407 (Ref. 21). During fixation, the cells are pressed onto the slide by centrifugal force. After fixation, the slide is separated from the chamber block and can then be processed by conventional staining techniques. The centrifugal cytology bucket was designed to facilitate the cytological examination of cells from dilute biological fluids.

The centrifugal cytology bucket can be used clinically to prepare cells for human screening (Ref. 22) and shows great potential for automated clinical cytology (Ref. 23). The Leif centrifugal cytology bucket has been used to prepare the following tissues and body fluids for cytological examination: blood (Ref. 19), cervical scrapes (Ref. 24), body fluids including cerebral spinal fluid (Ref. 25), nipple aspirate (Ref. 26), sputum (Ref. 25), urine (Ref. 27), eye fluids including tears and vitreous humor (Ref. 28). The centrifugal cytology bucket has been employed to quantitate biologically active lymphocytes, such as Jerne Plaque and rosette forming cells (Ref. 29), as well as natural killer cells (Ref. 30).

As described in U.S. Pat. No. 5,188,935 (Ref. 31), which is incorporated herein by reference, part or all of the staining of the cells can occur prior to sedimenting the cells onto the microscope slide. In the case of the Papanicolaou stain, it was possible (Ref. 32) to treat cervical-vaginal cells with two of the cystoplasmic stains (EA and OG), which were diluted in ethanol while they were still in the centrifugal cytology bucket. This was followed with a 100% ethanol wash, wash with a mixture of 50% ethanol and 50% xylene and a final wash with 100% xylene. After the addition of the EA and OG containing solution, "centrifugation was then omitted in order to minimize precipitation of the stain after this step." (Page 58). Complete dehydration of the cells prior to the addition EA and OG containing solution was necessary and required that the centrifugal cytology buckets be inverted. This procedure required significant manual labor, could not be directly automated, would require a complex mechanical system to invert the buckets, did not provide a complete solution to the problem of cross-contamination because the same pipette was used to add the solvents to the buckets, and provided minimal safety against the biohazards associated with human samples.

Van Duijn U.S. Pat. No. 4,192,250 (Ref. 33) has described a centrifuge with an electronically controlled valve that can empty the fluid from above a conventional microscope slide through a drainage channel and can overlay this surface with a fluid. This system has the following limitations: 1) The sample chambers are part of the rotor. This requires that the cover plate be removed in order to clean the inside of the chambers. Since the chambers are part of the rotor, they cannot be premanufactured to be both clean (cell free) and attached to the slide. Each slide has to be manually inserted with the cover plate removed. 2) Each chamber requires its own electronically controlled valve, which requires transfer of a significant amount of electricity to the rotor. The valves have to be opened for each transfer. 3) Because the valves have to repeatedly retard the fluid under full load, they can be caused to leak out the cell containing fluid by the presence of an imperfection or debris. 4) The system does not drain at rest. 5) The same type of fluid must be added to all of the chambers. This is a totally batch system, which does not include the capability to treat different slides with individualized reagents to simultaneously produce slides with different histochemistries. 6) The rotor can not be removed easily from the centrifuge for cleaning and maintenance. 7) The slide must be inclined at an angle of 4° to 6° with regards to the rotation axis, which in order to prevent sliding of the cells off of the slide, limits the centrifugal force applied. 8) Only one concentration of cells per unit area is produced on each slide. A new slide must be produced if the concentration of the cells on the slide is either too high or too low for analysis.

Kelly et al. U.S. Pat. No. 5,480,484 (Ref. 34) describes a cytology centrifuge apparatus that employs a cell concentrator assembly that is tilted at rest and is vertical in a rotor during centrifugation. In one of the embodiments three fluid specimens are inserted into three separate wells prior to centrifugation; and, in another embodiment, one larger specimen is inserted into one larger well prior to centrifugation. Fluid is transferred into the well(s) "by inserting a pipette containing the sample through the fluid receiving apertures". (Col. 8, lines 56-58) The orientation of the well(s) at rest is such that the cell containing fluid does not come into contact with the microscope slide. During centrifugation, the wells in the vertical cell concentrator assembly are in contact with the slide, which permits the cells to sediment on to the slide. After the centrifuge is stopped, the cell concentrator assembly returns to its tilted position and the supernatant liquid returns to the well(s) where it "may be removed by aspiration with a pipette inserted through the fluid receiving apertures". (Col. 9 lines 9-10) The cells subsequently can be stained in the cell concentrator assembly. "When the concentrator 70 is used as a staining chamber, staining reagents may be inserted into the wells 94a-c through the fluid receiving apertures 76a-c and brought into contact with the deposited cells by inverting the concentrator 70 so that so that the slide is resting in a horizontal orientation. With the concentrator 70 in this position, the reagents flow through the corresponding fluid expulsion apertures 90a-c, respectively, to contact and flow onto the slide 120. The concentrator 70 is effective as a staining chamber since there is no bibulous paper disposed between the chamber and the slide which would absorb the expensive staining reagents. Features of the concentrator 70 which enhance its use as a staining chamber include the shallowness and small volume capacity of the wells 94a-c which prevent waste of expensive staining reagents." (Col. 9 lines 31-42) This small volume capacity often makes it impossible to deliver from one centrifugation sample a sufficient number of cells for either research or clinical analysis. This problem is exacerbated by the necessity of stabilizing samples for shipment from the place where they were acquired to the clinical laboratory where they are prepared and analyzed. This stabilization of samples for liquid preparation often involves the dilution of samples with stabilizing fluids.

A series of patents, all assigned to E. I. Du Pont de Nemours & Co., describe vacuum driven means for the removal of supernatant fluid from removable chamber blocks that abut and are sealed by a deformable ring to a deposition surface. Boulclier, U.S. Pat. No. 4,306,514 (Ref. 35) and Boeckel, U.S. Pat. No. 4,327,661 (Ref. 36) described a removable chamber block that had an opening that received a cell suspension and contacted a deposition surface. A capillary, with an end proximal to the deposition surface, was connected to a vacuum line. After centrifugation has been completed, vacuum was applied and a baffle located just upfield of the capillary deflected the supernatant into a collection vial. This design "permits individual collection and segregation of supernatant withdrawn from the vicinity of the deposition surface."(Col. 8, lines 45-47) The use of a vacuum system significantly increases the cost and complexity of the device, as well as decreases its reliability. It also significantly increases the probability of air-drying of the cells, which causes a significant decrease in the quality of their morphology.

Boeckel et al. U.S. Pat. No. 4,314,523 (Ref. 37) describes a rotor and centrifuge combination that could be employed for the chamber blocks of U.S. Pat. No. 4,306,514 (Ref. 35) and U.S. Pat. No. 4,327,661 (Ref 36). The sample holder of U.S. Pat. No. 4,314,523 (Ref. 37) included a vacuum seal that permitted evacuating the chamber blocks while the rotor spun. This type of seal increases the cost and complexity of the device, as well as decreasing its reliability.

Boeckel et al. U.S. Pat. No. 4,423,699 (Ref. 38) described improvements on U.S. Pat. No. 4,314,523 (Ref. 37). The vacuum system was part of the top of the rotor and an improved spring loaded mechanism and pivot arm was employed to insert, hold and remove the sample containing chambers. The introduction of a staining dye through the tube that was connecting to the vacuum line was mentioned. This was a batch system, where all of the chambers and deposition surfaces would be exposed to the same dyes. The improvement of a rotating seal also was described.

Alternative embodiments of conduits that remove the supernatant from the chambers were described in FIGS. 4, 5, and 6 of U.S. Pat. No. 4,423,699. In FIG. 4, "the conduit 102 instead of being returned to the spring-loaded tube as described before, is simply brought back (radially inward) by the radial distance X and then returned (radially outward) to a point beyond the outer wall of the chamber such that once fluid fills the outlet portion of the chamber beyond the distance X, a fluid flow or siphon will be established which will be maintained until all the excess fluid is removed." (Col. 5, lines 21-28) This flow will occur during centrifugation and will remove all of the supernatant fluid. Although "a spring-loaded interconnector, of the type illustrated in FIG. 3, disposed in the outer wall of the rotor" (Col. 5, lines 29-31) is mentioned, no means is described on how to make this type of seal operate against a centrifugal force. It was also suggested, "Or, the outer wall and base of the rotor may be slotted to accommodate the exhaust conduit 102. In this instance, the exhausted fluid will atomize or "aerosol" within the housing (not shown) for the rotor." (Col. 5, lines 31-35) This would present an unacceptable biohazard.

FIG. 5 shows "an extra transport tube 120 is introduced with a deflector 122 at its outlet end so that fluid may be specifically introduced, from the upper portion 124 of the chamber, to fill the chamber with fluid to the distance X, following centrifugation and deposition on the slides, thereby to exhaust the chamber. The transport tube may be supplied from the distributor as in FIG. 1 using a spring-loaded contact,". (Col. 5, lines 37-44) This design will wash the chamber; however, it will not stop the premature loss of cell containing supernatant.

FIG. 6 shows the exhaust tube ending in a tee at the bottom of the chamber, with the upfield end being able to use a spring-loaded contact to connect through the rotating seal to a vacuum system to aspirate the fluid from the chamber or another unspecified source, to introduce fluid into the chamber. The possibility of using a double rotating seal to return the fluid in line 130 through the rotating seal to an exhaust chamber is mentioned. Presumably this would entail the same type of spring loaded seal as described for FIG. 4 with the same problem of maintaining a seal against the force of gravity. If this type of seal is not used, then again flow can occur during centrifugation with removal of cell containing supernatant fluid.

Wells U.S. Pat. No. 4,428,323 (Ref. 39) indicates that there was a significant problem with the supernatant leaving a chamber block prior to centrifugation. "Observations have indicated the possibility that a sample of particles and supernatant introduced into the inlet channel may run through the block into a collection vial before the particles have had an opportunity to deposit onto the deposition surface. This possibility is enhanced if withdrawal suction is applied to the block before the particles have been subjected to the centrifugal force field." (Col. 1, lines 42-49)

FIG. 1 of Wells U.S. Pat. No. 4,428,323 (Ref. 39) shows that the addition of a dam that defines a well for the supernatant solved this problem. However, the design shown in FIG. 1 limits the volume of sample, so that it is not suitable for cervical-vaginal and other cell suspensions of clinical interest. In order to be shipped from the physician to the clinical laboratory, these samples often have to be diluted into a stabilizing solution. Mechanical dissociation of these cells also requires a significant volume of fluid.

Wells U.S. Pat. No. 4,576,110 (Ref. 40) eliminated the use of a vacuum system by installing a channel ending in a porous plug, which was at a predetermined close distance from the cell deposition surface. The plug and cell deposition surface were separated from the cell deposition channel by dam. Initially, both the region of the chamber between the cell deposition surface and the plug are filled with air, which blocks the capillary transport of the cell containing fluid. Application of the centrifugal field results in moving the fluid over the dam to contact both the cell deposition surface and the plug. The patent states, "During rotation the centrifuge force acting in a radially outward direction relative to the rotor 10 overcomes the oppositely directed capillary force exerted by the absorbant plug P." (Col. 5, lines 15-19) The geometry of the cell containing fluid channel and the plug constitute a U tube and both are colinear with the centrifugal field. The two arms of the U tube will be brought into balance by the centrifugal field with the result that significant cell containing fluid could be lost or the volume of sample would be small and insufficient for many cytological preparations, such as cervical cytology preparations. In any event, after cessation of the centrifugal field, the downward inclination of the plug and capillarity should result in drainage of the supernatant fluid. The rotor was sealed, which will minimize the effect of internal aerosols, such as those produced by fluids draining out of the porous plug during centrifugation. Wells U.S. Pat. No. 4,574,729 (Ref. 41) commented on this possibility. "In practice, however, it has been found that while the centrifuge rotor rotates to its operating speed the presence of the absorbant plug in next adjacency to the deposition surface has the effect of prematurely withdrawing both supernatant and cells suspended therein. This is perceived as disadvantageous since it prevents the sedimentation of cells on the surface." (Col. 1, lines 43-49)

Wells U.S. Pat. No. 4,574,729 (Ref. 41) improved upon U.S. Pat. No. 4,576,110 (Ref. 40) by providing "a centrifugal force responsive arrangement which restrains the movement of the absorbent plug with respect to a chamber block in which it is inserted into the region in adjacency to the deposition surface until the rotor reaches a predetermined operating speed." (Col. 1, lines 58-62) This stops the premature loss of cell containing fluid. Two means to restrain the movement of the plug are described. The first employs a "flared portion at the trailing edge of the plug." (Col. 4, line 64) The tines which comprise this "flared portion" are compressed as the centrifugal force propels the plug into a cylindrical channel. The second means is essentially an O ring which is expanded by the plug. These plugs and housings are both complex and would require special instruments to remove them for the required cleaning, prior to reuse of the chamber blocks. The protruding of the trailing edge of the solid plug U.S. Pat. No. 4,574,729 (Ref. 41) can interfere with the removal of the chamber blocks from the rotor. U.S. Pat. No. 4,423,699 (Ref.

42) describes an "inner support for the back wall of the chamber and has a corresponding flat or planar portion 31 within each cavity adapted to accommodate the various chambers as described." (Col. 3, lines 49-53). Sliding the protruding trailing edge of a solid plug past a flat wall requires a complex mechanism to retract the wall.

Stokes et al., U.S. Pat. No. 5,376,267 (Ref. 43) describe an improved cytocentrifuge rotor that wets the filter pad prior to the arrival of the sample. A plurality of "liquid-receiving chambers are arranged in line successively to discharge sequentially into a conduit in common that leads to holding means for a filter pad", (Col. 1, lines 50-52) which terminates their cytocentrifigation device. The second chamber, which only holds "a few droplets of the wetting liquid, typically two-hundred microliters" (Col. 8, lines 2-4) is located above and opens into the conduit. Since the second chamber delivers its content directly into the conduit and is located between the sample chamber and the filter pad holder, the wetting liquid arrives at and wets the filter pad prior to the cell containing suspension. This significantly reduces the number of cells absorbed into the filter pad. The surface tension of the wetting liquid prevents movement in the conduit "except under centrifugal force when such liquid will flow toward and into the opening 12a or 27a of the filter pad in advance of the liquid sample from chamber 23." (Col. 8, lines 6-9).

FIG. 4 of U.S. Pat. No. 5,376,267 shows a third chamber for containing fixative. It is similar in size to and upfield of the sample chamber. The fixative chamber delivers its content to the conduit subsequent to the sample. No mention is made of the effect of the relative density of the fixative solution and that of the sample. If the fixative is less dense than the sample, it will float upfield of the sample; conversely, if it is more dense, it will sink downfield of the sample. If the fixative floats, its efficacy will be greatly diminished. If it sinks, the cells will be partially fixed as they traverse the fixative and proteins and other matter in the sample will be precipitated by the fixative and contaminate the surface of the slide. Since the conduit volume has to hold the sum of the volumes of the fixative and sample, the concentration of cells on the surface of the slide will be diminished. This decrease in cell concentration and limited deposition area of this cytocentrifugation device can result in a significantly reduced number of diagnostic cells, which renders the sample inadequate or suboptimal for diagnosis (Ref. 27). No means, other than the filter pad, was described to remove the fluid. Thus, this device is incapable of stopping the rotor and performing sequential additions of liquids.

Automated Staining Apparatus

Kalra et al. U.S. Pat. No. 5,948,359 describe (Ref. 44) an automated apparatus for staining cell and tissue specimens that is capable of random access and liquid coversliping a slide. This apparatus includes a unique arm that is movable in three dimensions and includes a hollow tip head. This head includes three channels, a wash tip, a blow tip and a reagent tip head. The reagent tip head "is adapted to pick up disposable plastic pipette tips from the standard containers". (Col. 4, lines 62-64) It can sample from multiple individual reagent vials and deliver a measured amount to individual microscope slides. The blow tip ends in a slit which delivers a stream of gas, typically air, that removes excess liquids from a microscope slide. The wash tip which "is used to deliver diverse liquid solutions to the slide." (Col. 5 lines 29-30).

U.S. Pat. No. 5,948,359 (Ref. 44) states (Col. 16, lines 38-41), "Representative of protocols useful in such slide preparation protocols are the methods disclosed in PCT Publication WO 95/24498 and in U.S. Pat. No. 5,578,452 (Ref. 45)." U.S. Pat. No. 5,492,837 (Ref. 46) states, "Accordingly to our invention, aqueous PVP (polyvinyl-pyrrolidone) is employed as a mounting medium for hematological, histological and cytological microscope slide preparations and for any other slide mounting situation involving tissue and blood preparations." (Col. 2, lines 38-42)

Stokes et al., U.S. Pat. No. 5,180,606 (Ref. 47) have described a staining apparatus that includes a slide holding carousel, which can be interchanged "with a different, interchangeable centrifuging rotor," (Col. 4, lines 43-44). The cells have been deposited on standard microscope slides prior to the insertion of the slides in the carousel. The microscope slides are held in the carousel with the long dimension of the slide surface oriented in the direction of the centrifugal field and the shorter dimension of the slide surface vertical. Reagents are sprayed through nozzles against the slide surface that has the deposited cells. One nozzle, "however, is arranged to spray the back side of the slides as they pass." (Col. 7, lines 12-13) "The carousel is operated at a known rate of rotation, for example, thirty RPM, for the spraying operation." (Col. 6, lines 41-43) In a description of the use of crystal violet as part of the gram staining protocol, U.S. Pat. No. 5,180,606 states, "It has been found that a ten second spray time (five full revolutions of the carousel) is generally satisfactory." (Col. 6, lines 55-57) The continuing discussion of the method states, "After application of the crystal violet, it has been found beneficial to increase the speed of rotation of the carousel to between 500 to 1000 RPM for three seconds to remove the excess crystal violet reagent from the slides." (Col. 6, lines 62-66)

The application of the centrifugal field is orthogonal to slide surface that has the deposited cells, which results in a force to shear the cells from the slide. The reagents are applied in batch mode. Although U.S. Pat. No. 5,180,606 employs flow control valves which can "be operated to conserve all reagents by controlling the spray of reagent to spray only during the time the slides present in the carousel are passing the spray nozzles when less than a full load of slides is being stained", (Col. 6, lines 20-24) no means is provided or mentioned to selectively apply a reagent to a subset of the slides in the carousel without cross-contamination. Since the reagent is applied continuously, the amount of reagent is greater than that required to just wet the surface of the slide. The use of fixed nozzles, to apply reagents to rotating slides, results in an aerosol, which, as is shown in FIG. 2 of U.S. Pat. No. 5,180, 606, is only contained by a top cover, which must eventually be opened. There is a running collecting area through circumferentially placed slots, which are located at the bottom portion of the carousel into drain fitting 38 in the bowl beneath the carousel, which is connected by tubing to an exit drain fitting at a lower level in instrument housing.

Centrifugal Driven Dispensing Systems

Centrifugal driven dispensing systems previously have been employed in chemistry analyzers, for example U.S. Pat. No. 3,856,470 (Ref. 48) and U.S. Pat. No. 4,431,606 (Ref. 49). As described in U.S. Pat. No. 3,856,470, each member of a pair of radially spaced chambers can be loaded with a separate fluid, such as a reagent in one chamber and an analyte containing solution in the other chamber. Centrifugal force delivers the two solutions to a third chamber where they are mixed and subsequently delivered into a cuvette for optical analysis. U.S. Pat. No. 4,431,606, which is incorporated herein by reference, describes an analytical centrifugal rotor which permits precise distribution of identical volumes into analytical cells for subsequent optical measurements of analytes through the windows of the analytical cells. This analytical centrifugal rotor includes: a common central distribution chamber, portioning cavities, two or more overflow reservoirs, and analytical cells. The common central distribution chamber is filled with a volume of liquid that is greater than the sum of the volumes of the analytical cells. The excess volume of liquid is transferred to the overflow reservoirs. This is accomplished by the employing a transfer passage, which acts as a synthetic boundary valve, that blocks fluid transfer at low centrifugal forces "of the order of 400 to 600 rpm for 4 to 8 s." (Col. 3, lines 22-23); but permits liquid transfer from the common central distribution chamber to the portioning cavities, and subsequently transfer of the excess liquid through apertures into the overflow reservoirs. Rapidly increasing the centrifugal force "to 4,000-5,000 rpm for 2-5 seconds" (Col. 3, line 51) breaks the meniscus and both allows the escape of air and entrance of fluid through the transfer passage of the analytical cells.

SUMMARY OF THE INVENTION

A centrifugal cytology system for monolayering materials, such as cells and/or small particles onto the surface of a microscope-type slide receiving surface member, which is removably mounted vertically on the downfield side of a chamber block. An array of chamber block assemblies are positioned around the periphery of a rotor capable of precise indexing and rotation at sufficient speed to sediment material. These chamber block assemblies receive sample and treating agent liquids in batch and/or random access mode, from dispensers adjacent to the rotor. Treating agent gases are received by being released at a higher pressure at one location and removed at a lower pressure at another location. Vacuum can be applied by sealing the higher pressure location and creating a vacuum at the lower pressure location. Sample is input directly into the cavity of the chamber block assembly; and then a centrifugal field is applied to sediment the sample as a monolayer onto the surface of the receiving surface member. The chamber block assembly has a drain port provided with a centrifugal force responsive valve, which opens after the centrifugal force is applied. Preferably, the cavity of the chamber block assembly contains a volume decreasing element, which decreases the sedimentation path length adjacent to a portion of the deposition surface; whereby, that portion's monolayer of sample is of decreased concentration, as compared to the remainder of the deposition surface's monolayer.

The system includes a circular array of treating agent (liquid) holding troughs, one respective trough being upfield of each chamber block assembly. By centrifugal force, each trough feeds its treating agent into the upfield side cavity of the chamber block assembly, for flowing that treating agent downfield and against the sample monolayer previously formed on the receiving surface member. When the rotor is slowed and then stopped, the liquid treating agent flows out through the previously opened valve port. A sequence of treating agents thus can be applied to the monolayer of sample, to treat the sample and prepare it for analysis. Subsequently, the receiving surface member is separated from the chamber block for analysis and storage. In one embodiment, each treating agent trough is unified with a chamber block. In another embodiment, the rotor carries a treating agent (liquid) holding ring which empties into the troughs. In both embodiments, the chamber block assemblies are individually removable from the rotor. In a third embodiment, a thin walled insert containing multiple chamber blocks can be inserted into a special rotor.

It is therefore an object of the invention to provide an automated specimen processor, for preparing fixed monolayers of stained cells, that allows automated staining of individual receiving surface members, including microscope slides with different combinations of stains and/or treating agents, with minimal or preferably no user intervention, including where appropriate the application of a liquid coverslip.

It is a further object of this invention to provide an automated specimen processor that uses treating agents, including expensive staining treating agents, efficiently with a minimum of waste and without extraneous steps.

It is a still further object of this invention to include in this specimen processor the capability to be an automated monolayer forming apparatus, that can perform additional steps as part of a completely automated staining protocol.

It is a still further object of this invention to minimize cell loss in any and all steps in preparing fixed, monolayers of stained cells on receiving surface members, including microscope slides.

It is a still further object of this invention to provide an automated specimen processor that minimizes the risk of cross-contamination between receiving surface members, including slides, treating agents and solutions.

It is also an object of this invention to minimize the cost of the preparation of fixed monolayers of stained cells on individual receiving surface members, including microscope slides, by automation of the entire process.

It is yet a further object of this invention to deposit simultaneously at least two monolayers of different concentrations on different surface areas of a receiving surface member.

BRIEF DESCRIPTION OF THE DRAWINGS

FIGS. 6A-D are side views of the chamber block assembly, showing movement of treating agent induced by application of a centrifugal field;

DESCRIPTION OF PREFERRED EMBODIMENTS

Figure 1:
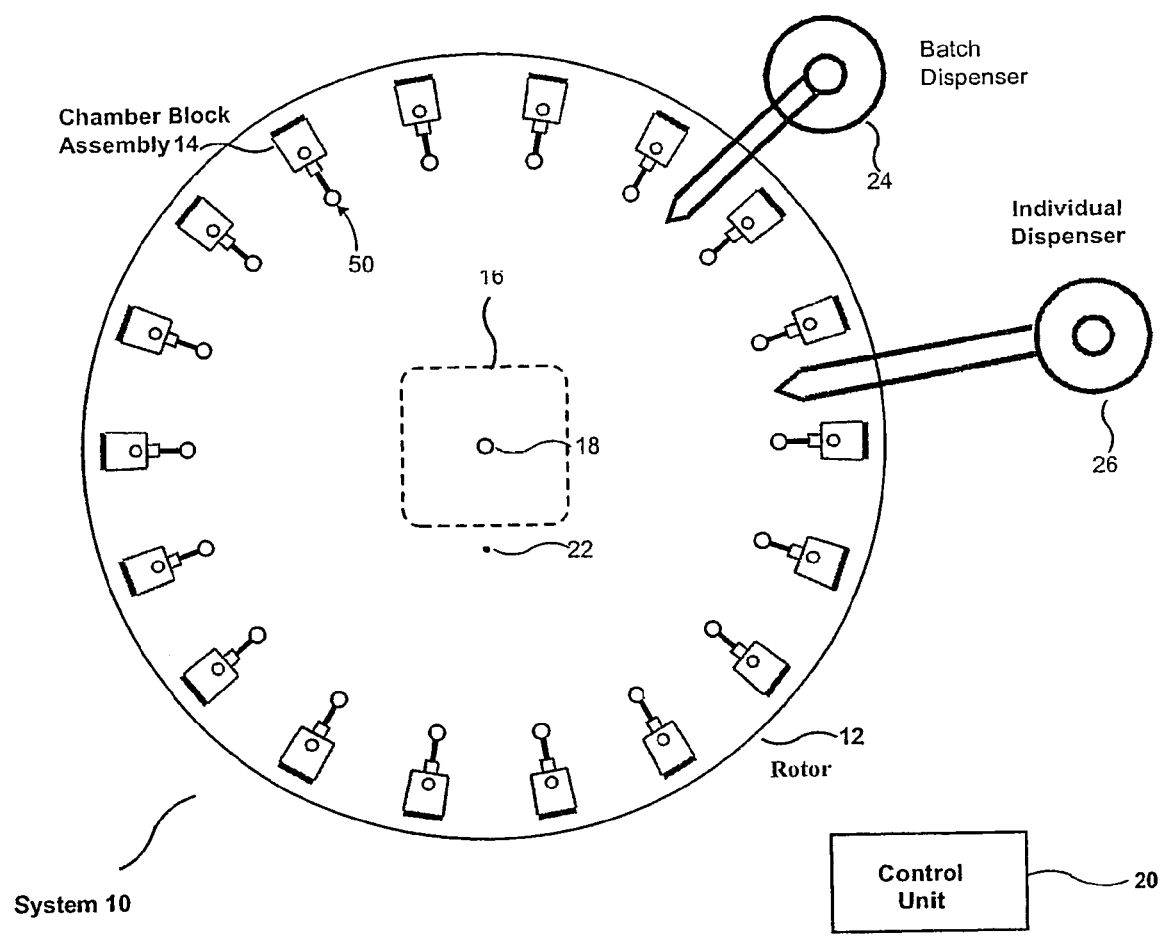
FIG. 1 is a diagrammatic top view of the centrifugal cytology system.

Referring to FIG. 1, the centrifugal cytology system is identified generally by numeral 10. The centrifugal cytology system includes a rotor 12 that holds a plurality of individual, removable chamber block assemblies 14, arranged in the form of an array at the circumference of rotor 12 and is driven by a motor 16 (shown in dashed lines), of which the shaft 18 is shown. The rotor 12 is precisely indexed by the motor 16 and a control unit 20. The combination of the motor 16 and a control unit 20 provide both precise indexing and a rotational speed to develop 50×gravity or more. In the preferred embodiment, the motor 16 is equipped with an optical encoder or other means that will provide position information. The motor 16 can be a servomotor or in an alternative embodiment a multipole stepper motor, with or without micro-stepping.

One or more cylindrical holes 22 provides for drainage of waste fluids from the bottom of the rotor. The same or different treating agents can be delivered to each of the chamber block assemblies 14. One or more batch dispensers 24 delivers the same treating agent to each of the chamber block assemblies 14; and zero or more optional individual treating agent dispensers 26 can provide random access capability by delivering a treating agent to an individual chamber block.

Figure 2:
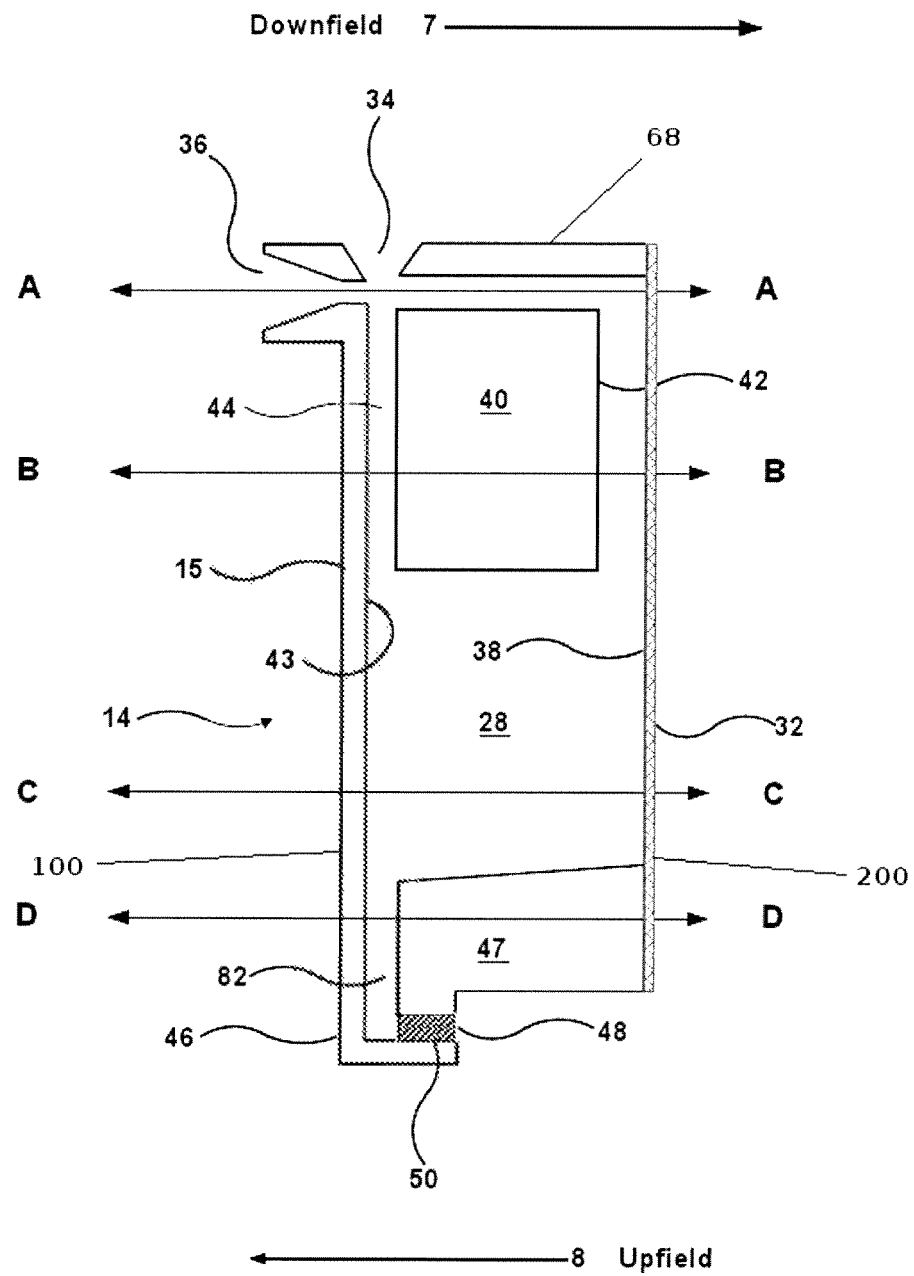
FIG. 2 is a side view of a chamber block assembly.
Figure 3A:
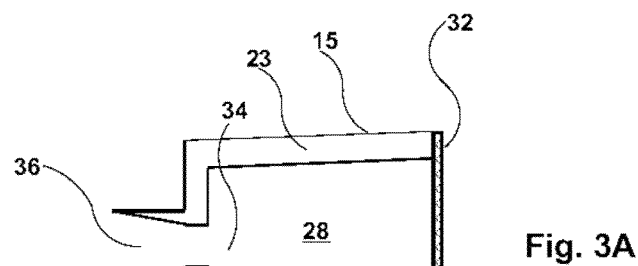
FIGS. 3A-D are top views of thin slices of the chamber block assembly, cut along lines A-A, B-B, C-C and D-D of FIG. 2.

A chamber block assembly 14 is shown in FIG. 2 and as thin sliced top views in FIGS. 3A, B, C and D. In FIG. 2, as well as other figures when appropriate, the spatial orientation of the chamber block in the centrifugal field is indicated by downfield arrow 7 and upfield arrow 8. In contradistinction to the original centrifugal cytology swinging bucket U.S. Pat. No. 4,250,830 (Ref. 4), the chamber block assemblies 14 are maintained in a fixed position by the rotor. Each chamber block assembly comprises a cavity 28, a chamber block 15, and a receiving surface member or slide 32; on to which is to be deposited the materials such as cells or particles present in the sample. Cavity 28 is defined by the top and bottom of the chamber block, as well as the upfield side wall 100, opposing sidewalls 23 and 25, and either a receiving surface member 32 or a downfield sidewall 200. Where as receiving surface member 32 is used, the receiving surface member 32 functions, among other things, as a downfield sidewall. The chamber block 15 can be fabricated out of a solvent resistant plastic, such as polymethylpentene, Mitsui Chemicals America, Inc, Purchase, N.Y.

Figure 3B:
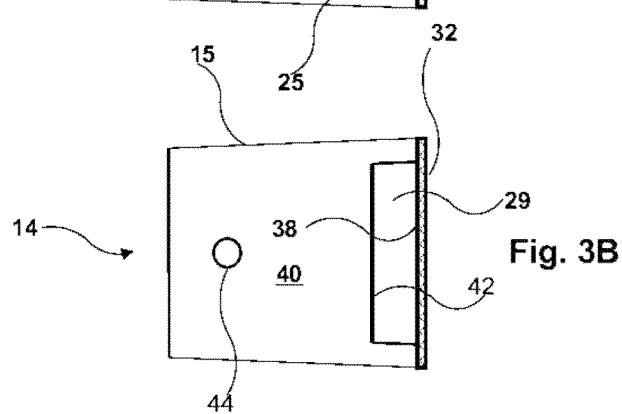
Figure 3C:
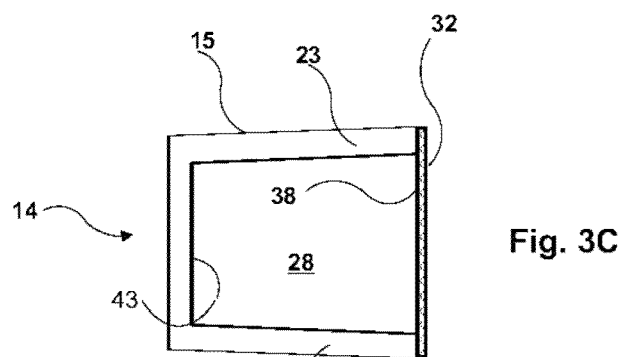

The centrifugal cytology system 10 causes the cells to be deposited as one or more monolayers 30, 30•• in a fixed orientation on the receiving surface member or slide 32 (see FIG. 4C); and also has the capability to add and remove treating agent fluids from each chamber block assembly 14. A sample inlet 34 is located at the top of the chamber block 15 towards the center of the rotor 12. A separate treating agent inlet 36 is located at the upfield side, near or at the top of the chamber block. FIG. 3A is a top view along line A-A of FIG. 2, which shows both the location of the sample inlet 34, and the treating agent inlet 36 and the full cavity 28. The chamber block 15 preferably includes a means to produce two or more different concentrations of a material, such as cells or other particles, on a slide or receiving surface member 32. As is shown in FIG. 3B, a view along line B-B of FIG. 2, a reduced volume cavity 29 results when the chamber block 15 includes a volume reducing element 40, which shortens the distance between the upfield side of the cavity 42 and the cell or particle receiving surface 38 of the receiving surface member 32. This reduction in cavity 28 significantly decreases the volume of fluid per unit area of the cell or particle receiving surface 38 of the receiving surface member or slide 32. As is shown in FIG. 3C, a view along line C-C of FIG. 2, absence of the reducing element 40 maximizes the volume of cavity 28 and concurrently the volume of fluid per unit area of the cell or particle receiving surface 38 of the receiving surface member or slide 32.

Figure 3D:
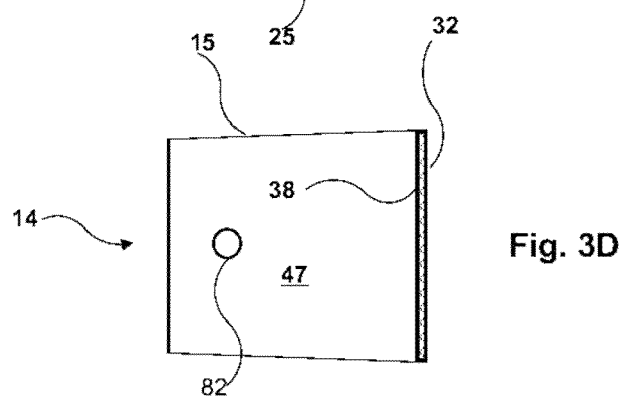

As is shown in FIG. 3D, a view along line D-D of FIG. 2, the bottom 47 of the chamber block 15 seals against the cell or particle receiving side 38 of the receiving surface member 32, which closes the bottom of the chamber block assembly. A cylindrical channel 44 conveys the sample from the sample inlet 34 of FIG. 2 through the volume reducing element 40 of FIG. 3B into the cavity 28 to a protuberance 46, which is part of the bottom 47 of the chamber block 15. This protuberance 46 contains a plug 48, fit into an output port 50 that faces in the downfield direction. This plug 48 is to be removed by the action of the centrifugal field, as is shown in FIG. 4B.

The receiving surface member 32 and the chamber block 15, when joined together, serve as a liquid containing module, the chamber block assembly 14. The receiving surface member and chamber block are bonded in such a manner that they can be separated easily. This bond could be: a weak adhesive, such as employed in 3M Post-it®, St. Paul, Minn.; a silastic or other adhesive that can be cut or preferentially bind to one surface; a grease such as Plews Multi-Purpose Grease, Plews/Edelman Division, Stant Corporation, Dixon, Ill. 61021; or a material, such as a wax, that can be melted at moderate temperatures. U.S. Pat. No. 5,784,193 (Ref. 50), which is incorporated herein by reference, teaches the use of a microscope slide to which is bonded a removable layer with one or more openings for cells or other materials. Another approach to producing a bond between the receiving surface member 32 and the chamber block 15 is to employ a two-pour mold to manufacture the chamber block 15. The first pour can consist of a thin (0.1 to 2 mm) film of an elastomer; and the second pour can be the rest of the chamber block 15. Both the durability and ease of breaking this bond are critical. The chamber block assembly 14 must not leak; yet, the chamber block 15 and the receiving surface member 32 must be separated after they leave the centrifugal cytology system, so that the material, such as cells or particles, on the surface 38 can be analyzed and/or the receiving surface member 32 stored.

Figure 4A:
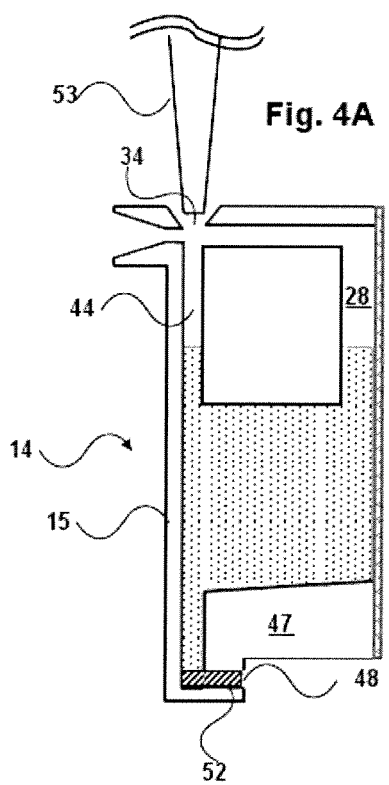
FIGS. 4A,B are side views of the chamber block assembly, showing movement of sample induced by a centrifugal field.
Figure 4B:
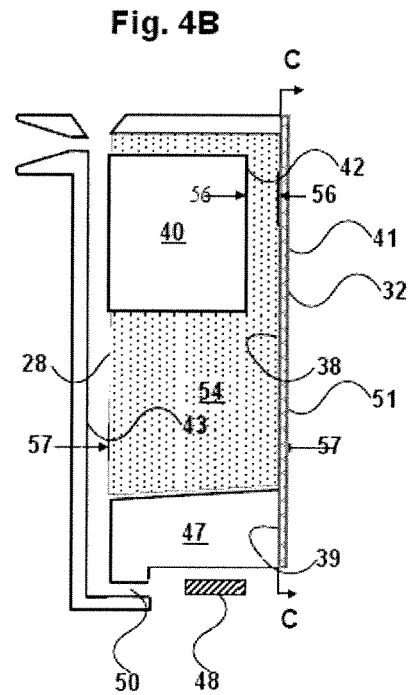
FIG. 4C is a view of the particle/cell receiving side of the receiving surface member, along line C-C of FIG. 4B, showing sedimented cells.

FIG. 4A depicts the transfer of the material, such as a cell or particle containing sample, into the chamber block assembly 14. A sample injector 53 is lowered into the sample inlet 34 of the chamber block 15. A volume of sample suspension is injected through sample inlet 34 and the cylindrical channel 44 into the cavity 28, also shown in FIG. 2. After the sample injector is elevated to remove it from the chamber block 15, the rotor 12 is accelerated to produce a centrifugal field sufficient to form a monolayer of sedimented cells onto the receiving surface 38 of receiving surface member 32, and to propel the plug 48 out of the port 50, as shown in FIG. 4B. While the centrifugal field is applied, the bulk if not all of the sample suspension 54 remains in the chamber block assembly 14. After sufficient time has elapsed to sediment the materials, such as cells or other particles, onto the material receiving side 38 of the receiving surface member 32, the rotor 12 is decelerated and stopped. The sample suspension fluid drains from the port 50 during deceleration and while the rotor is at rest, leaving the cavity 28 empty, except for a monolayer of material and accompanying thin layer of suspension fluid that has attached to the material receiving side 38 of the receiving surface member 32. This returns the chamber block assembly 14 to the same condition as in FIG. 2, except that plug 48 has been removed and the attachment of the material to the surface of the slide or receiving surface member.

The concentration of the sedimented material is proportional to the sedimentation path length. This path length can be decreased by the use of a volume decreasing spacer 40, which extends the upfield side 43 of the cavity 28 of the chamber block 15 in the downfield direction. The distance 56 between the downfield side 42 of the volume decreasing spacer 40 and the area 41 of the opposing receiving side 38 of the receiving surface member 32 is less than the distance 57 between the upfield side 43 of the sample suspension 54 and the area 51 of the opposing receiving side 38.

Figure 4C:
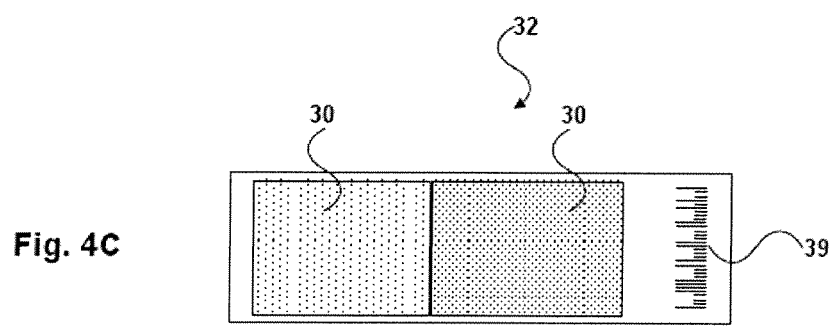

FIG. 4C is a view along line C-C of FIG. 4B. Since the concentration of material 30 and 30•• on the receiving side 38 of the receiving surface member 32 (FIG. 4C) is proportional to the effective width of the cavity 28, i.e. the sedimentation path length, the concentration in area 41 is less than that in area 51. This creation of two different concentrations of material 30, 30•• increases the probability that an area with an optimal material concentration will be produced. Use of multiple volume/path decreasing means will permit multiple concentrations of a material, such as cells or particles, to be created on opposing portions of the surface 38 of receiving surface member 32. Also, as shown in FIGS. 4B and 4C, the receiving surface member 32 can include a barcode 39 or other means to identify the source of the material.

Individual types of synthetic boundary valves 52 can be designed for a specific centrifugal force. The design of a specific type of valve can be specified to open at a specific centrifugal force. The present, preferred embodiment of the valve 52 (FIG. 4A) is a simple drill hole or port 50 (FIG. 4B) that is filled with grease forming the plug 48. The position, diameter, length of the drill hole 50 can be modified to increase or decrease the field necessary to open the valve 52. The viscosity of the grease and its adhesion to the walls of the drill hole both increase the force necessary to dislodge it from the drill hole to thereby open the valve. The temperature of the centrifuge can also be increased, which will decrease the viscosity of the grease or even melt the grease, and thus facilitate its removal. It should be noted that the operation of the centrifugal cytology system 10 is substantially independent of the centrifugal field necessary to open the synthetic boundary valve 52 because the bulk of the fluid only escapes after the rotor has been decelerated and is approaching rest. For most practical purposes, a releasing field of between 5 and 500 times gravity is acceptable. However, there can be specific applications were a very low field, between 2 and 5 times gravity, would be necessary, because the product of the centrifugal force and time is being minimized to decrease the relative concentration of small particles on the receiving side 38 of the receiving surface member 32.

The production of monolayer dispersions of small particles, such as viruses or bacteria or chromosomes, is facilitated by employing centrifugal forces that are greater than that presently used for cells (100 to 1,000×gravity). Centrifugal cytology system rotors 12 which operate at these higher centrifugal fields can employ synthetic boundary valves which open at higher centrifugal forces. It also should be noted that there is a possible advantage of employing the centrifugal field of this invention to deliberately flatten the cells. If this can be accomplished without distorting the internal morphology of the cells, then the quality of the diagnostic images should be improved. Increasing the area of the individual cells and decreasing the out-of-focus material, by decreasing the thickness of the cells, should both improve the image.

The initial centrifugation of the material onto the material receiving side 38 of the receiving surface member 32 encompasses two aspects. The first aspect is to sediment the material on to the receiving side 38 of the receiving surface member, and the second is to cause the material to bind or adhere to this surface 38. This binding of the material to the surface 38 depends upon the chemistry of the receiving surface member and/or its surface. Positively charged species or physically binding agents have been demonstrated to increase the adherence of cells to conventional microscope slides (Ref. 6, Ref. 51). In the case of fixation or staining, the time for performing each step is based on the chemistry of the step.

The centrifugal cytology system 10 can have two types of dispensing systems, batch and random access. The batch dispensing system dispenses to all of the chamber blocks 15 of the chamber block assemblies 14 common solutions, such as: fixatives, wash solutions, alcohols, stains, mounting media, etc.

FIGS. 5 A-D are partial side views, which show in progression the transfer of treating agents from the batch dispenser 24 of FIG. 1 and the individual dispenser 26 of FIG. 1 to a treating agent trough 58. FIG. 5A shows an area of the rotor 12 directly upfield from the chamber block 15. Going in the direction upfield to downfield, the top 60 of the rotor 12 is configured to produce a treating agent ring 62, followed by the treating agent trough 58, which is at a greater depth in the rotor. The downfield upper edge of the treating agent trough has a lip 64 which meets the upfield front wall 66 of the chamber block 15.

Figure 5A:
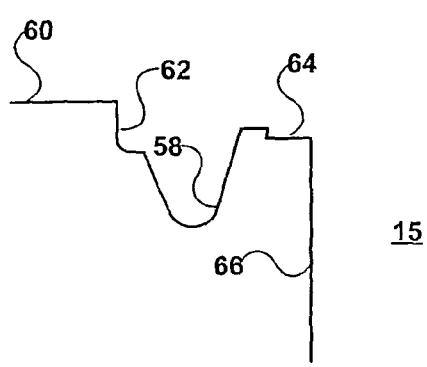
FIGS. 5A-D are progressive side views of the downfield portion of the rotor and upfield top portion of the chamber block.
Figure 5B:
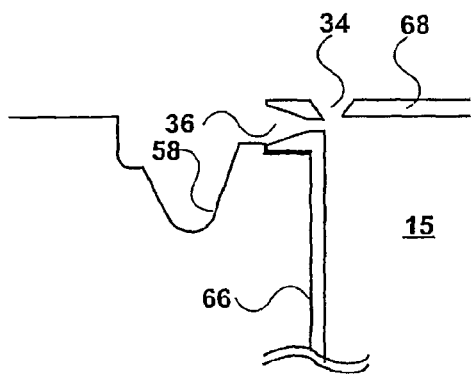

FIG. 5B shows part of the upfield wall 66 and part of the top 68 of a chamber block 15, which has been inserted in the rotor 12 of FIG. 1. The treating agent inlet 36 is located near and downfield from the treating agent trough 58. The sample inlet 34, which is not involved in this portion of the total process, is shown in the upfield part of the top 68.

Figure 5C:
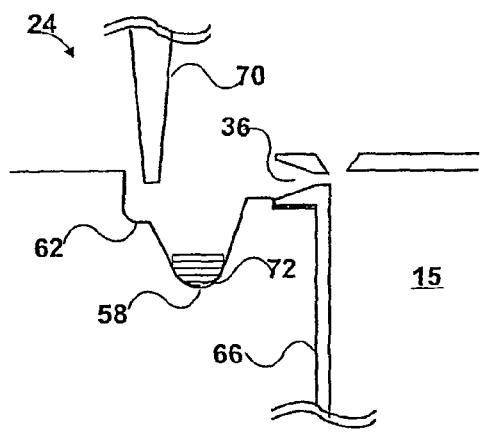

As is shown in FIG. 5C, the tip 70 of the batch dispenser 24 is in position to deliver a treating agent fluid into the treating agent ring 62.

Figure 5D:
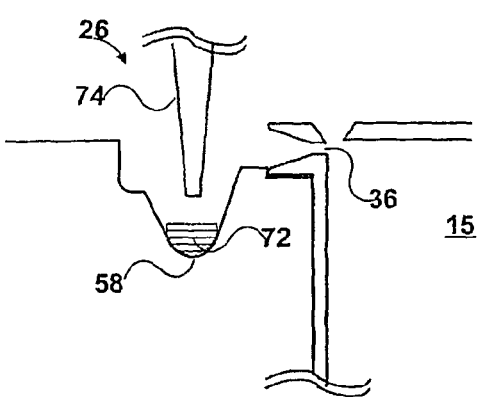

The individual dispensers 26 of FIGS. 1 and 5D are for treating agents that are to be used for one or more, but conventionally not all of the chamber block assemblies 14 arrayed at the circumference of the rotor 12. These individual dispensers can consist of an arm capable of vertical motion (not shown) and will be equipped with a treating agent dispensing means. The technology of random access delivery of treating agents is well developed. The mechanism for treating agent transfer to the chamber block assemblies 14 could be in a manner similar to that employed for the Coulter$^R$ DACOS$^R$ chemistry analyzer (U.S. Pat. No. 4,234,539 Ref. 52). U.S. Pat. No. 4,234,539 described a treating agent supply area that had separate treating agent containers located in a treating agent disc. treating agent dispensers added "appropriate reagents to specific cuvettes as those cuvettes advance around the path of movement of the annular array." (Col. 5, lines 25-27) The control unit 20 shown in FIG. 1 could index the rotor 12 to place a chamber block assembly 14 underneath an individual treating agent dispenser 26 of FIG. 1, which has previously been filled with a treating agent from a separate treating agent container. As described in Hoskins et al. (U.S. Pat. No. 3,883,305 Ref. 53), the aliquot and diluent transfer mechanism, as well as the treating agent dispensers, can be of the type and operate as disclosed with reference to FIGS. 13c and 16 of U.S. Pat. No. 3,883,305, which is incorporated herein by reference. An alternative design for liquid transfer has been described by Kelln et al., (U.S. Pat. No. 5,334,349, Ref. 54), which is incorporated herein by reference. Such transfer dispensers would swing arcuately between the source of the sample or treating agent and a chamber block assembly 14. Both, when receiving and dispensing fluid, the probe of the dispensers can move down into the treating agent containers (not shown), a material suspension (not shown), a treating agent ring 62 or treating agent trough 58 (FIG. 5), but would be elevated to be able to swing free thereof in an arcuate path. In an alternative embodiment, each individual treating agent dispenser 26 could included a prefilled individual container, which if necessary could be kept at constant temperature.

The individual dispensers 26 are located around the rotor 12 above a stopping position for a chamber block assembly 14. Since the rotor 12 can index any chamber block assembly 14 to any dispenser location, random access is provided for: special solvents, special stains, monoclonal antibodies, nucleic acid probes, liquid coverslipping material and other treating agents. FIG. 5D shows the rotor at rest. An individual dispenser tip 74 has been lowered into a treating agent trough 58 and the liquid treating agent 72, after being pumped through the individual dispenser tip 74, is located at the bottom of that treating agent trough 58. The pool of the treating agent fluid 72 produced by this random access process in the treating agent trough 58 is approximately the same volume and at the same location as that delivered by the batch dispenser 24 for batch treating agents. If the same treating agent were delivered by one or more individual dispensers 26, the system could function in batch mode.

FIGS. 6A-D show the movement of the treating agent fluid 72 in the chamber block assembly 14. After the treating agent is in the treating agent trough 58 of FIG. 5 and the rotor 12 is accelerated to produce a centrifugal field sufficient to transfer the treating agent 72 from the treating agent trough 58 through the treating agent inlet 36 and then, as shown in FIG. 6A, into an upper channel 78 in the cavity 28. As is shown in FIG. 6B, under the influence of the centrifugal field, a thin layer 80 of the treating agent 72 is formed on the material receiving side 38 of the receiving surface member 32. FIG. 6C is an enlargement of a portion of FIG. 6B, showing the layering 80 of the treating agent 72 on the material receiving side 38 of the receiving surface member 32. After the treating agent has had sufficient time to interact with the monolayers of material, such as 30, 30•• shown in FIG. 4C, which are present on the receiving side 38 of the receiving surface member 32, rotor 12 is decelerated and brought to rest. As shown in FIG. 6D, this results in the treating agent fluid 72 flowing to the bottom of the chamber block 15 and exiting through a bottom channel 82 and then through the output port 50.

Liquid coverslips are an example of a treating agent which does not need to exit the chamber block assembly 14. Instead, they harden into a thin refractive index matching coating under the influence of a centrifugal force. This hardening can be accelerated by the application of vacuum and/or heat. Three examples of liquid coverslips that could be used with the present invention are a commercially available mounting medium, such as Clearium® Surgipath Medical Industries Inc., Richmond Ill., an aqueous polyvinyl-pyrrolidone solution (Ref. 46) and a transparent plastic with a high refractive dissolved in an organic solvent, such as Zeonor® 1020R, Zeon Chemicals L.P., Louiseville, Ky.

Figure 7:
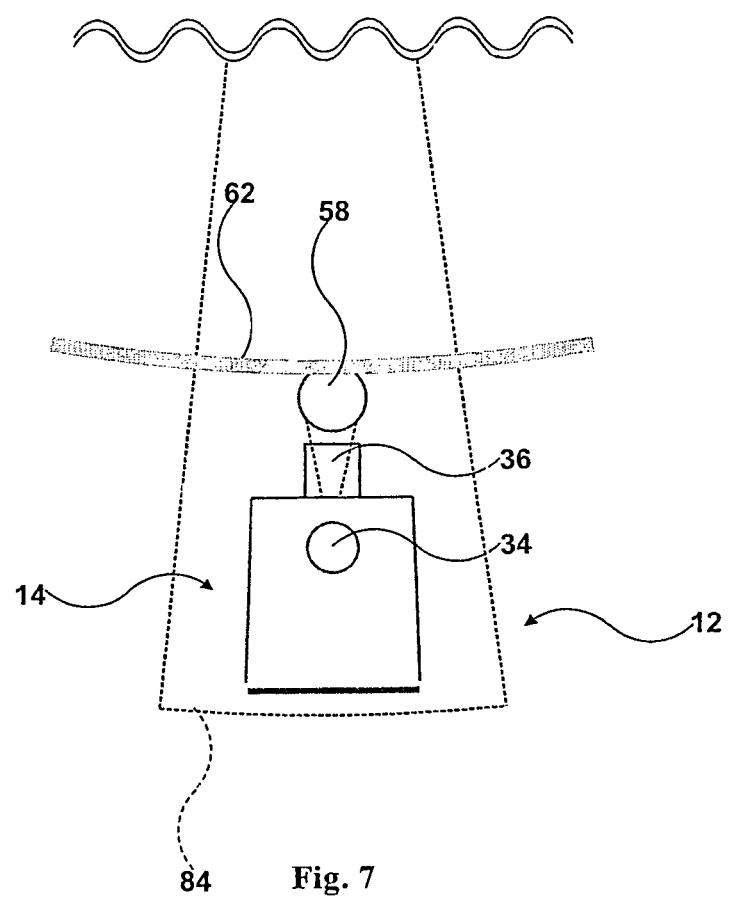
FIG. 7 is a top view of an area showing an embodiment of the rotor.

FIG. 7 shows part of a sector 84 of a rotor 12 with an included chamber block assembly 14. The assembly 14 receives the treating agent fluid 72 from a treating agent trough 58 that is integral with the rotor 12. The treating agent fluid 72 is delivered by the tip 70 of the batch dispenser 24 into the treating agent ring 62 of FIG. 5C. This delivery can be accomplished quickly by simultaneously rotating the rotor 12 to produce approximately one times gravity or less and pumping the treating agent through the batch dispenser tip 70 of FIG. 5C. When the treating agent pumping rate and the velocity of the rotor are appropriately adjusted, the treating agent fluid will be continuously and evenly delivered to the treating agent ring 62. The treating agent fluid in the treating agent ring 62 then is directed by the combination of gravity and centrifugal field into each treating agent trough 58. The pool of the treating agent fluid 72 produced by this batch process in the treating agent trough 58 is approximately the same volume and at the same location as that delivered by the individual dispenser 26 of FIG. 1, for random access treating agents. If necessary, the precision of this delivery of the same treating agent to more than one chamber block assembly 14 can be improved by employing the technology described in U.S. Pat. No. 4,431,606 (Ref. 49).

The use by many cytochemical and histochemical procedures and staining protocols of mixtures of varying ratios of solvents, such as ethanol and water or ethanol and xylene, has required that each of these mixtures be stored in its own container. This creation and storage of these mixtures is expensive in terms of both time and space. These mixtures can be formed by mixing the output of two or more pumps as the solvents are delivered. The delivery rates of each pump can proportional to the final concentration of its solvent in the final solution. For instance, two small motor driven gear pumps operated at equal rates will provide a 50 percent solution. If the ethanol pump is on and the water pump is off, pure ethanol will eventually result. The ethanol and xylene pumps can then deliver solvent at the same rate and produce a 50 percent mixture, which can be followed by pure xylene. If necessary, the output of the pumps can be mixed by a helix, which is well known in the art.

Figure 8A:
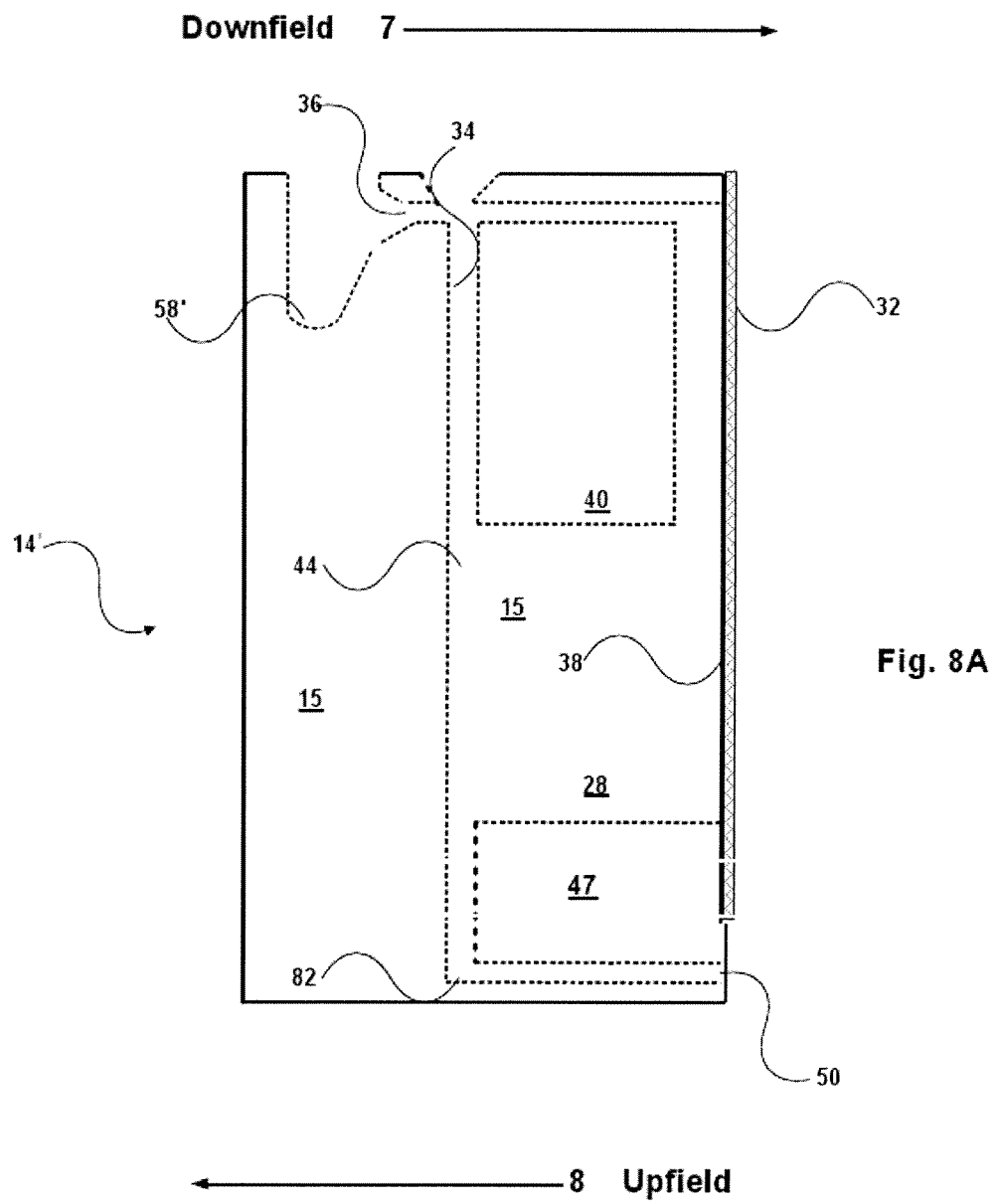
FIGS. 8A and 8B are side and top views of an alternative design of the chamber block assembly.
Figure 8A:
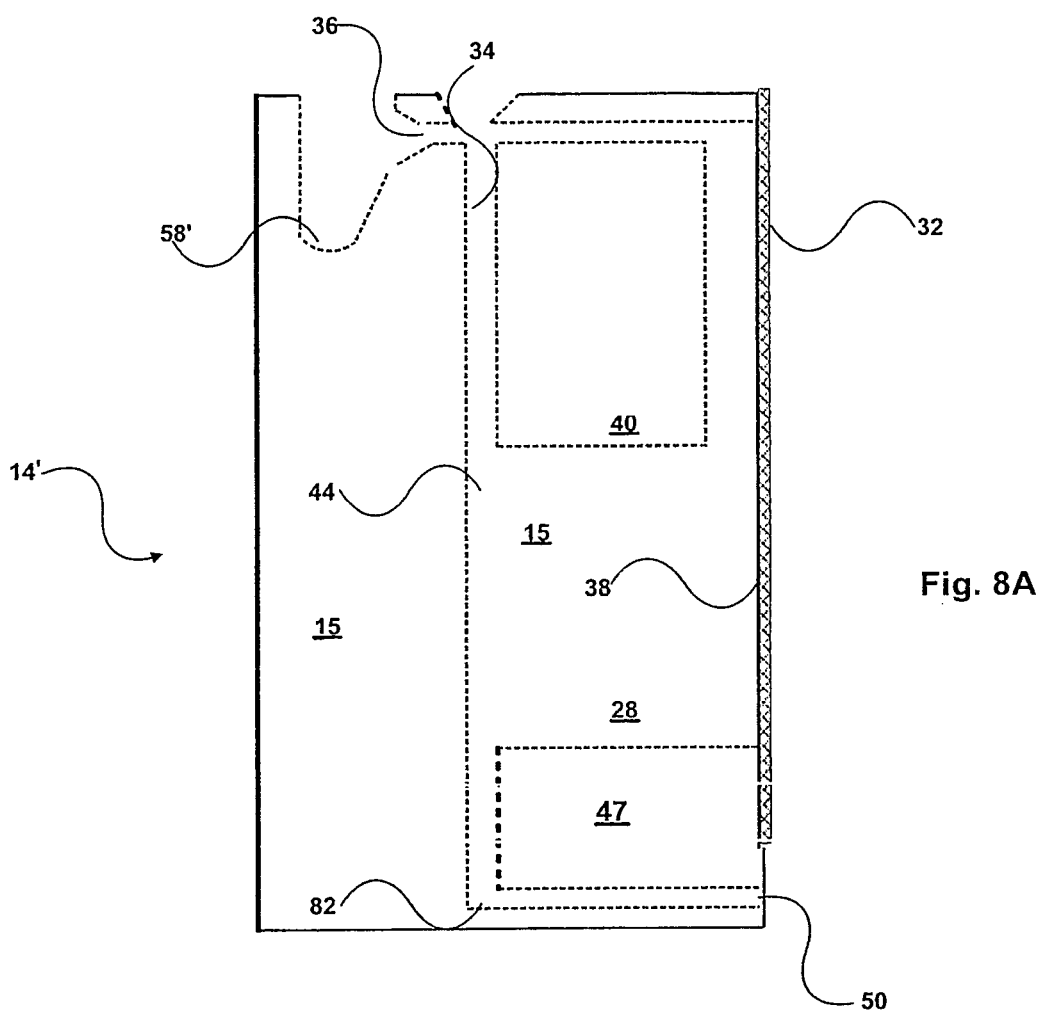
Figure 8B:
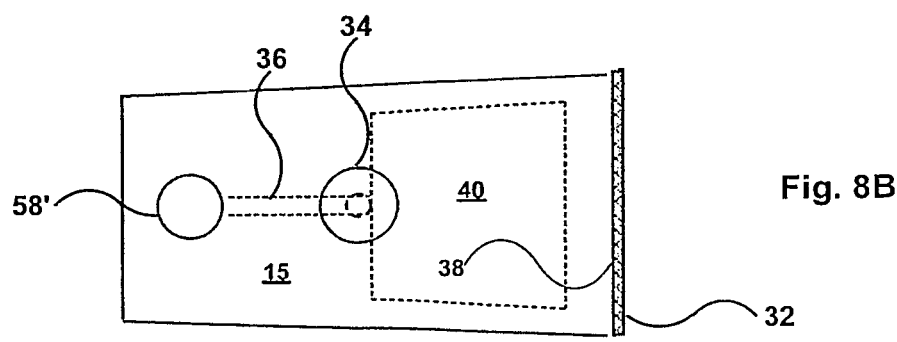

FIG. 8 shows an alternative chamber block assembly 14•• design, with the treating agent trough 58•• being an integral part of the chamber block 15. FIGS. 8A and 8B are respectively side and top views. The sample inlet 34 is located at the top and at approximately the center of the chamber block 15. The treating agent trough 58•• is located at the upfield side, at the top of the chamber block. As previously described, while the rotor is at rest, a treating agent is dispensed into the treating agent trough; then, while the rotor is rotating, the treating agent is first transferred by the centrifugal field into the treating agent inlet 36 and subsequently to the receiving side 38 of the receiving surface member 32; and finally, while the rotor is decelerating or finally at rest, the treating agent exits through channel 82 and then through the output port 50. The sample inlet 34 is not part of this process, but has been included for purposes of orientation.

An alternative embodiment of the system 10 is possible. Each of the treating agent dispensers 26 could be located in a fixed horizontal position and be movable in the vertical direction. The treating agent dispenser remains sufficiently above the rotor to provide clearance, except during a filling cycle, when the appropriate chamber block assembly 14 is indexed to be in its position. The treating agent dispenser then would be lowered from its rest position and deliver a measured amount of treating agent to the treating agent trough 58. As stated above, a treating agent dispenser 26 could include its own prefilled individual container.

Two or more pipeters also could be employed to dispense individual treating agents in batch mode. In that case, there is up to one syringe and/or pipettor for each chamber block assembly. These pipeters can be driven by a common actuator. Peristaltic pumps also can be employed to dispense the individual solutions.

Standard robotic equipment and procedures can be employed to insert and remove the array of chamber block assemblies 14 and/or one or more of the of the chamber block assemblies 14 into and from the rotor 12; as can manual handling. Subsequently, the receiving surface member 32 can be separated from the chamber block assembly so that the monolayer then can be analyzed and/or the member 32 be stored.

The processing of the Centrifugal Cytology System can be accelerated by the treatment of the treating agents overlaying the materials with microwave energy Ref. 55; or the combination of microwave energy and pressure Ref. 56.

The hereinabove provided specification, along with the figures, are believed to be more than sufficient to enable one skilled in the art to practice the invention, including modifications, adaptions and enhancements, without departing from the spirit and scope of the hereinafter presented claims and any subsequent amendments thereto.

What is claimed is:

1. A chamber block for use in a centrifugally operating system for preparing treated monolayers of sample material, said chamber block comprising:
   a top and a bottom;
   first and second opposing side walls extending between said top and bottom at opposing sides thereof and attached to said top and bottom;
   an upfield side wall, the upfield side wall extending along a centrifugal up field side of said chamber block and extending between said top and bottom, and extending between said first and second opposing side walls, and attached to said top and bottom;
   an output drain port positioned proximate said bottom and down field of said centrifugal upfield side wall; and
   a centrifugally operated valve for opening said output drain port,
   said top comprising a sample material input wall;
   said upfield side wall and said top defining an opening therebetween, the opening being a treating agent input,
   wherein said top, bottom, first and second opposing side walls, and upfield side wall define an interior cavity of said chamber block, said interior cavity being open at a down field side thereof, said down field side adapted to receive in fluid sealing engagement a removable receiving surface member
   the removable receiving surface member having a surface area and forming a downfield side wall of said chamber block extending between said first and second opposing side walls, a substantial portion of the entire surface area of the receiving surface member contacting said interior cavity.

2. A chamber block according to claim 1, in which:
   said valve is constructed and arranged to open during a time when sample material is being sedimented by centrifugation, as a monolayer, upon said receiving surface member.

3. A chamber block according to claim 2, in which:
   said valve is a plug inserted into said drain port.

4. A chamber block according to claim 1, further including:
   a receiving surface member in fluid sealing engagement with a down field edge of each of said first and second opposing side walls of said chamber block, a substantial area of said receiving member bounding said interior space of said chamber block.

5. A chamber block according to claim 1, the chamber block affixed to a surface of a rotor of a centrifugally operated system, said chamber block oriented such that said treating agent input substantially faces a center of said rotor,
wherein the rotor comprises a treating agent holding trough, positioned up field of said treating agent and in treating agent centrifugal flow connection therewith.

6. A plurality of chamber blocks according to claim 1, adapted to be removably arrayed circumferentially around the exterior of a rotor of a centrifugally operable system;
   said chamber blocks being mechanically and fluidically isolated from one another;
   whereby sample material fed into said sample material input of one of said chamber blocks will not be cross-contaminated with sample material in a different chamber block;
   and treating agent fed into said treating agent input will not be cross-contaminated with treating agent in a different chamber block.

7. A plurality of chamber blocks according to claim 1, said chamber blocks adapted to be removably arrayed circumferentially around the exterior of a rotor of a centrifugally operated system;
   said rotor having a plurality of radially positioned treating agent troughs, isolated from each other and each radially alignable up field of one of said treating agent inputs, for centrifugal transfer of treating agent into a respective one of said chamber blocks.

8. The device according to claim 7 wherein the plurality of chamber blocks are arranged circumferentially around the exterior of the rotor of the centrifugally operated system, further comprising:
   an indexer for aligning a specific one of said chamber blocks and its specific one of said treating agent troughs with a treating agent dispenser, prior to the centrifugal transfer of treating agent.

9. A chamber block according to claim 4, further comprising a volume reducing element positioned within said block and defining at least two paths of different lengths between said sample material input and said receiving surface member.

10. A chamber block according to claim 4 wherein a treating agent provided via said treating agent inlet is dispensed to said receiving surface member in a single centrifugation of said chamber block.

11. A chamber block according to claim 1 wherein said chamber block is affixed to a centrifuge rotor, and further wherein said output drain port remains open after a single centrifugation when said centrifuge rotor is at rest.

12. A chamber block to claim 1 wherein said chamber block is affixed to a centrifuge rotor, and further wherein said chamber block is substantially fixed in position on said rotor.

13. A chamber block for use in a centrifugally operating system for preparing treated monolayers of sample material, the chamber block comprising:
   a top and a bottom;
   a centrifugal upfield side wall and a centrifugal downfield side wall, said centrifugal upfield side wall and centrifugal downfield side wall extending between said top and said bottom and attached to said top and said bottom;
   first and second opposing side walls, said first and second opposing side walls extending between said top and bottom and attached to said top and bottom;
   said top comprising a sample inlet proximate said upfield side wall;
   said upfield side wall and said top defining an opening therebetween, the opening being a treating agent inlet, the sample inlet and treating agent inlet having substantially differing paths,
   wherein said top, bottom, upfield side wall, downfield side wall, and first and second opposing side walls define an interior cavity of said chamber block, said cavity being directly connected to said sample material input, said chamber block being adapted proximate a downfield side thereof to receive in fluid sealing engagement a surface of a removable receiving surface member;
   an output drain port positioned proximate said bottom and down field of said upfield side wall and connected to said cavity;
   a centrifugally operated valve for opening said outlet drain port;
   a receiving surface member in fluid sealing engagement with said chamber block proximate said downfield side thereof, a substantial area of a surface of said receiving member bounding said interior cavity of said chamber block;

the chamber block affixed to a surface of a centrifugally operated system, the treating agent inlet in fluid communication with said cavity and in fluid communication with at least one troughs in a rotor upfield of said cavity, the sample inlet in fluid communication with a vertical channel that makes direct contact with the interior cavity of said chamber block.

14. The device according to claim 1, wherein the surface of the centrifugally operated system is the surface of a rotor, the rotor comprising a treating agent holding trough at an upfield side of said chamber block and upfield of said treating agent inlet, the treating agent inlet in centrifugal flow connection therewith.

* * * * *